United States Patent
Hayashi

(10) Patent No.: US 9,615,734 B2
(45) Date of Patent: Apr. 11, 2017

(54) OPHTHALMOLOGIC APPARATUS

(71) Applicant: KABUSHIKI KAISHA TOPCON, Itabashi-ku (JP)

(72) Inventor: Takefumi Hayashi, Wako (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 287 days.

(21) Appl. No.: 14/585,431

(22) Filed: Dec. 30, 2014

(65) Prior Publication Data

US 2015/0208916 A1 Jul. 30, 2015

(30) Foreign Application Priority Data

Jan. 28, 2014 (JP) .................. 2014-013143

(51) Int. Cl.
*A61B 3/10* (2006.01)
*A61B 3/00* (2006.01)
*A61B 3/15* (2006.01)
*A61B 3/113* (2006.01)

(52) U.S. Cl.
CPC .......... *A61B 3/1005* (2013.01); *A61B 3/0025* (2013.01); *A61B 3/0083* (2013.01); *A61B 3/102* (2013.01); *A61B 3/113* (2013.01); *A61B 3/152* (2013.01)

(58) Field of Classification Search
CPC ... A61B 3/0025; A61B 3/1005; A61B 3/1015; A61B 3/102; A61B 3/117; A61B 3/14; A61B 3/145; A61B 3/15; A61B 3/152
USPC ................ 351/204, 205, 206, 210, 212, 246
See application file for complete search history.

(56) References Cited

U.S. PATENT DOCUMENTS

| | | | |
|---|---|---|---|
| 2007/0236661 A1 | 10/2007 | Fukuma et al. | |
| 2008/0151188 A1 | 6/2008 | Kawai et al. | |
| 2013/0235343 A1* | 9/2013 | Hee ........................ | A61B 3/102 351/206 |

FOREIGN PATENT DOCUMENTS

| | | |
|---|---|---|
| JP | 2007-275375 | 10/2007 |
| JP | 2008-161218 | 7/2008 |

* cited by examiner

*Primary Examiner* — Huy K Mai
(74) *Attorney, Agent, or Firm* — Oblon, McClelland, Maier & Neustadt, L.L.P.

(57) ABSTRACT

In an embodiment, a photographing part of an ophthalmologic apparatus photographs an eye from different directions. An optical system splits light into measurement light and reference light and detects interference light of measurement light returned from the eye and reference light. A changing part changes optical path length of measurement light. A controller controls the photographing part to perform photography and the optical system to perform first detection when first optical path length is set and controls the optical system to perform second detection when second optical path length is set and a second image substantially the same as a first image acquired by the photography is acquired. Based on the first and second optical path lengths, a calculator calculates distance between first and second sites of the eye through which measurement light has passed in the first and second detections, respectively.

24 Claims, 12 Drawing Sheets

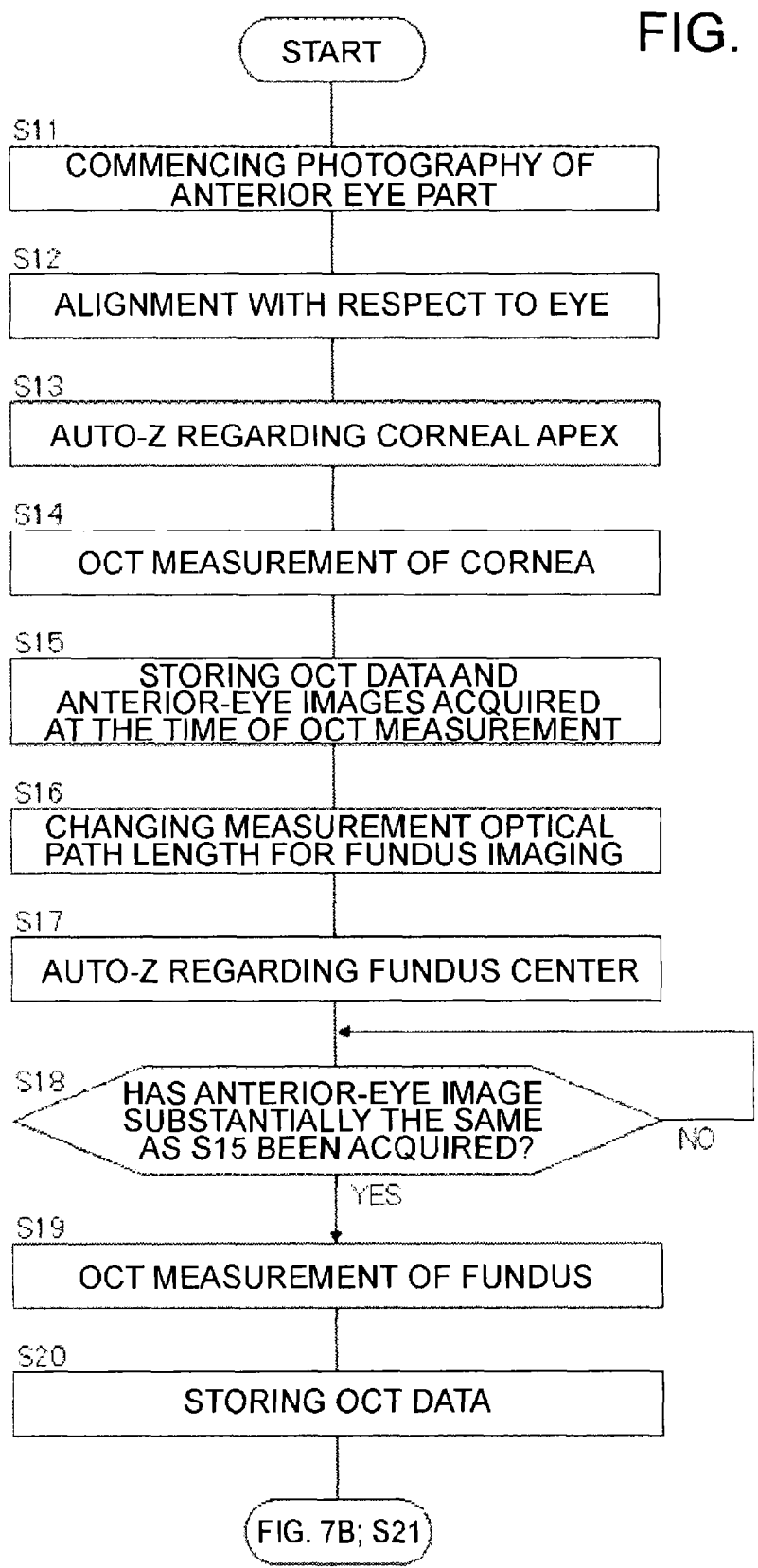

OPHTHALMOLOGIC APPARATUS

TECHNICAL FIELD

The present invention relates to an ophthalmologic apparatus for measuring distance in an eye.

BACKGROUND TECHNOLOGY

Distance in an eye is one of important parameters for ophthalmologic diagnosis. For example, axial length that indicates distance between a cornea and retina is used in diagnosis of axial myopia and axial hypermetropia. Further, locations (relative locations with respect to a characteristic site of the eye, for example) and sizes (distance from one end to the other end, for example) of lesions are also important information for making diagnostic decision. Hereinafter, such a distance in an eye is sometimes referred to as an "intraocular distance". Known methods of measuring intraocular distances include methods using ultrasounds and methods using optical coherence tomography (OCT).

PRIOR ART DOCUMENT

Patent Document

[Patent Document 1] Japanese Laid-open Patent Publication No. 2008-161218
[Patent Document 2] Japanese Laid-open Patent Publication No. 2007-275375

SUMMARY OF THE INVENTION

Problem to be Solved by the Invention

When intraocular distances are measured by means of OCT, it is necessary to individually detect returned light of measurement light from the respective two sites (first and second sites) that become both ends of this distance. Such detecting actions are classified into simultaneous detection and non-simultaneous detection.

In the case of the simultaneous detection, an optical configuration for forming two reference optical paths corresponding to returned light from two sites is needed. For example, such a configuration includes a first reference mirror for forming a first reference optical path corresponding to returned light from the first site, a second reference mirror for forming a second reference optical path corresponding to returned light from the second site, and a driving mechanism for moving the first and second reference mirrors independently. In this manner, the simultaneous detection has disadvantage that configurations of apparatuses become complicated and large.

On the other hand, in the case of the non-simultaneous detection, detection of returned light from the first site and detection of returned light from the second site are carried out at different timings from each other; therefore, there is a risk that position or direction of an eye could change between these detections. In this way, non-simultaneous detection has disadvantage that accuracy of measurement is lowered.

The objective of the present invention is to provide an ophthalmologic apparatus capable of measuring intraocular distances with high accuracy and without increasing size and complexity of the apparatus.

Means for Solving the Problem

An ophthalmologic apparatus of an embodiment includes: a photographing part that photographs an eye from two or more different directions; an optical system that splits light from a light source into measurement light and reference light and detects interference light of returned light of the measurement light from the eye and the reference light; a changing part that changes optical path length of the measurement light and/or the reference light; a controller that controls the photographing part to perform photography and the optical system to perform first detection when first optical path length is set by the changing part and controls the optical system to perform second detection when second optical path length is set and a second image that is substantially the same as a first image acquired by the photography is acquired by the photographing part; and a calculator that calculates distance between a first site of the eye through which the measurement light has passed in the first detection and a second site of the eye through which the measurement light has passed in the second detection based on the first and second optical path lengths.

Effect of the Invention

According to ophthalmologic apparatuses of embodiments, it is possible to measure intraocular distances with high accuracy while not increasing sizes and complexities of the apparatuses.

BRIEF EXPLANATION OF THE DRAWINGS

FIG. 7A is a flowchart showing an operation example of an ophthalmologic apparatus according to an embodiment.

MODES FOR CARRYING OUT THE INVENTION

Examples of embodiments of ophthalmologic apparatuses related to the present invention are explained in detail with reference to diagrams. Ophthalmologic apparatuses related to embodiments function to measure intraocular distance by means of OCT. In this specification, an image obtained by optical coherence tomography is sometimes referred to as an OCT image. Further, a measuring action for forming an OCT image is sometimes referred to as an OCT measurement. It should be noted that the contents of the documents cited in this specification may be employed in the following embodiments.

In the following embodiments, OCT apparatuses using OCT of so-called spectral domain type are described; however, the present invention may also be applied to OCT apparatuses using different types from spectral domain, such as swept source type and en-face type. It should be noted that the swept source OCT is a method of imaging morphology of an object by: scanning (sweeping) wavelengths of light irradiated to the object; acquiring spectral intensity distribution by successively detecting interference light obtained by superposing the reflected light of the light of the respective wavelengths on reference light; and executing Fourier transform on the acquired spectral intensity distribution. The en-face OCT is a method of forming an image of a cross-section (C cross-section) of an object orthogonal to travelling direction of light by irradiating light having a predetermined beam diameter to the object and analyzing the components of interference light obtained by superposing reflected light thereof and reference light, and it is also referred to as full-field type.

A combined apparatus of an OCT apparatus and a retinal camera is explained in the following embodiment; however, applications of the present invention are not limited to such combined apparatuses. For example, the present invention may be applied to apparatuses with other combinations or ophthalmologic OCT apparatuses with a single function. Examples of the combined apparatuses include a combined apparatus of an OCT apparatus and an SLO (scanning laser ophthalmoscope), a combined apparatus of an OCT apparatus and a slit lamp microscope, a combined apparatus of an OCT apparatus and an operation microscope, and the like. Further, the present invention may be applied to combined apparatuses of three or more apparatuses.

<First Embodiment>
[Configuration]

Figure 1:
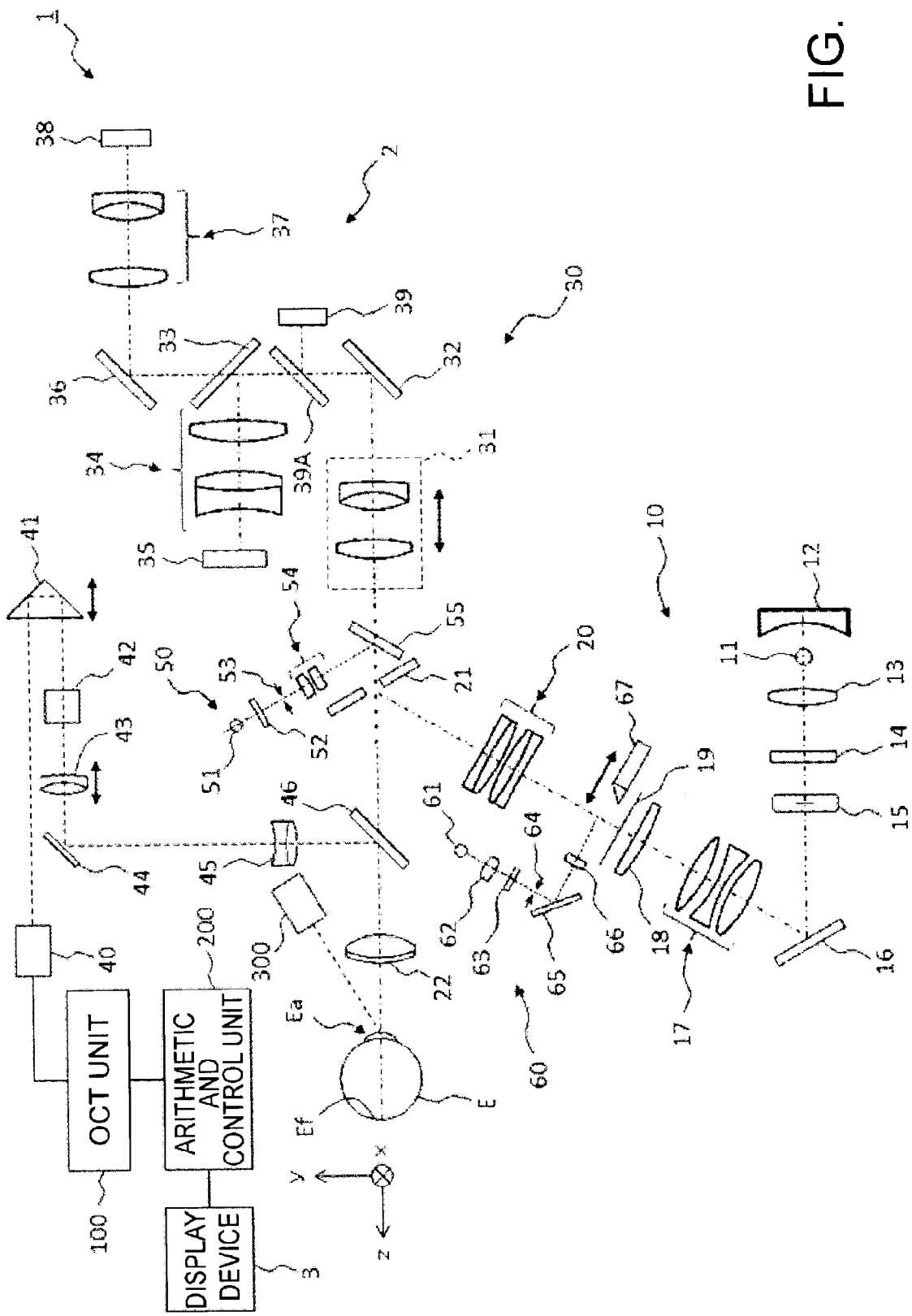
FIG. 1 is a schematic diagram showing an example of the configuration of an ophthalmologic apparatus according to an embodiment.

As shown in FIG. 1, an ophthalmologic apparatus 1 includes a retinal camera unit 2, an OCT unit 100 and an arithmetic and control unit 200. The retinal camera unit 2 includes almost the same optical system as conventional retinal cameras. The OCT unit 100 is provided with an optical system for acquiring an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for acquiring two-dimensional images (fundus images) presenting morphology of the surface of a fundus Ef of an eye E. Fundus images include observation images, captured images, etc. The observation image is a monochrome moving image formed with a preset frame rate using near-infrared light, for example. It should be noted that when the optical system is focused on an anterior eye part Ea of the eye E, the retinal camera unit 2 may acquire an observation image of the anterior eye part Ea. The captured image is a color image captured by flashing visible light or a monochrome still image using near-infrared light or visible light as illumination light, for example. The retinal camera unit 2 may be capable of acquiring other types of images such as fluorescein angiography images, indocyanine green fluorescent images and autofluorescent images.

Figure 4A:
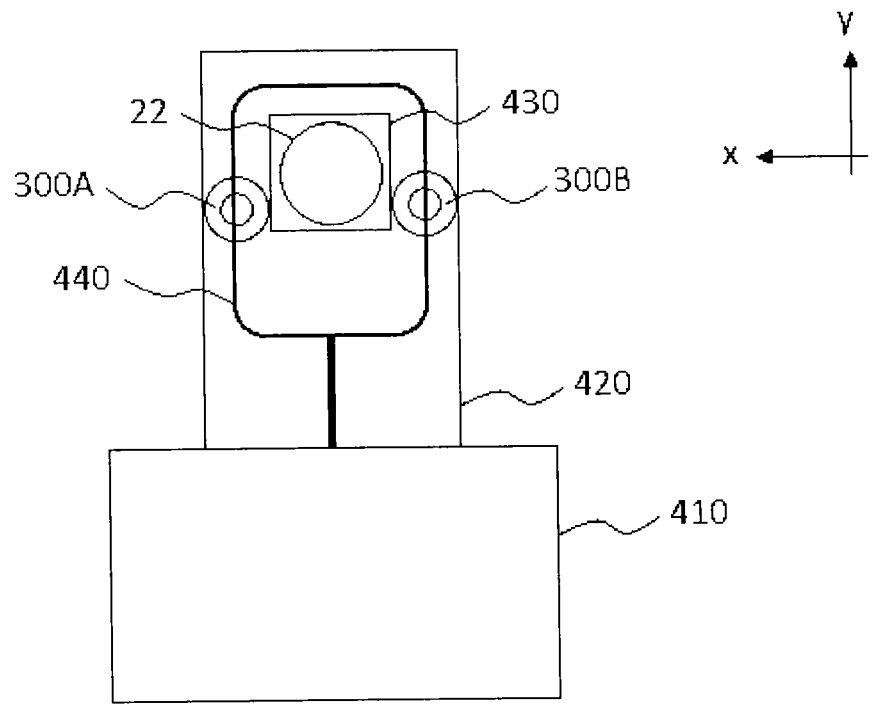
FIG. 4A is a schematic diagram showing an example of the configuration of an ophthalmologic apparatus according to an embodiment.
Figure 4B:
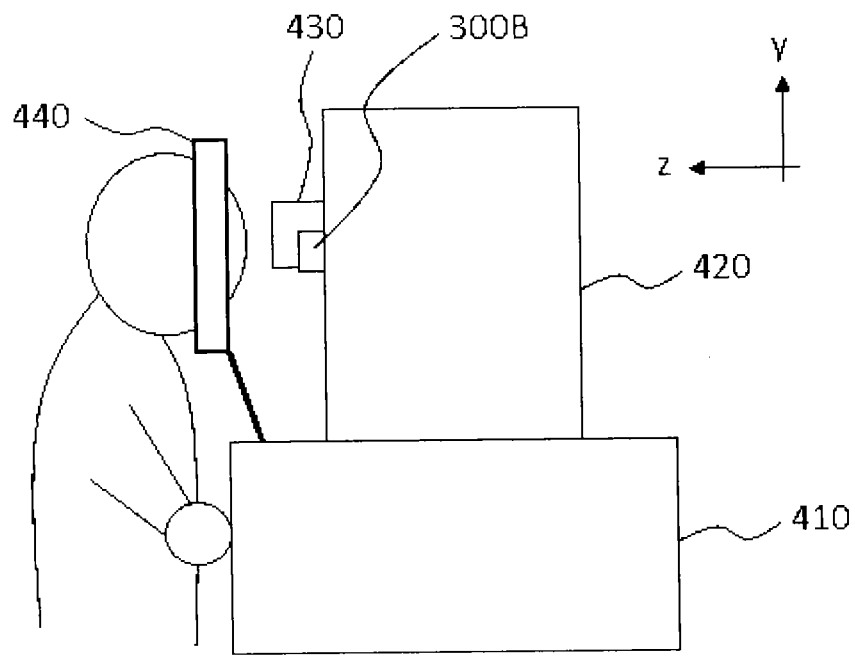
FIG. 4B is a schematic diagram showing an example of the configuration of an ophthalmologic apparatus according to an embodiment.

A jaw holder and forehead rest for supporting a face of a subject is provided with the retinal camera unit 2. The jaw holder and forehead rest correspond to a supporter 440 indicated in FIGS. 4A and 4B. In FIGS. 4A and 4B, a symbol 410 indicates a base in which a driving system such as an optical system driver 2A and arithmetic and control circuits are accommodated. A symbol 420 indicates a case that is provided on the base 410 and accommodates optical systems. A symbol 430 indicates a lens case that is provided as a protrusion from a front surface of the case 420 and accommodates an objective lens 22.

The retinal camera unit 2 is provided with an illumination optical system 10 and an imaging optical system 30. The illumination optical system 10 irradiates illumination light to the fundus Ef. The imaging optical system 30 guides reflected light of the illumination light from the fundus to imaging devices (CCD image sensors (sometimes simply called CCD) 35, 38). Moreover, the imaging optical system 30 guides measurement light from the OCT unit 100 to the fundus Ef and guides the measurement light via the fundus Ef to the OCT unit 100.

An observation light source 11 in the illumination optical system 10 includes an LED (light emitting diode) or a halogen lamp, for example. Light output from the observation light source 11 (observation illumination light) is reflected by a reflection mirror 12 with a curved reflection surface, passes through a condenser lens 13 and passes through a visible cut filter 14 to become near-infrared light. Further, the observation illumination light is once converged near an imaging light source 15, reflected by a mirror 16 and passes through relay lenses 17 and 18, diaphragm 19 and relay lens 20. Then, the observation illumination light is reflected on a peripheral part (surrounding region of an aperture part) of an aperture mirror 21, penetrates a dichroic mirror 46, and refracted by the object lens 22, thereby illuminating the fundus Ef.

Fundus reflection light of the observation illumination light is refracted by the object lens 22, penetrates the dichroic mirror 46, passes through the aperture part formed in the center region of the aperture mirror 21, passes through a dichroic mirror 55, travels through a focusing lens 31, and reflected by a mirror 32. Further, the fundus reflection light passes through a half-mirror 39A, is reflected by a dichroic mirror 33, and forms an image on a light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. It should be noted that when the imaging optical system 30 is focused on the anterior eye part, an observation image of the anterior eye part of the eye E is displayed.

The imaging light source 15 includes an LED or a xenon lamp, for example. Light output from the imaging light source 15 (imaging illumination light) is irradiated to the fundus Ef through a similar route to the observation illumination light. Fundus reflection light of the imaging illumination light is guided to the dichroic mirror 33 through the same route as that of the observation illumination light, passes through the dichroic mirror 33, reflected by a mirror 36, and forms an image on a light receiving surface of the CCD image sensor 38 by a condenser lens 37. An image (captured image) based on the fundus reflection light detected by the CCD image sensor 38 is displayed on the display device 3. It should be noted that the display device 3 for displaying an observation image and the display device 3 for displaying a captured image may be the same or different. Further, when similar photographing is carried out by illuminating the eye E with infrared light, an infrared captured image is displayed.

An LCD (Liquid Crystal Display) 39 may display fixation targets and visual targets for measuring visual acuity. The fixation targets are visual targets for fixating the eye E and used in fundus photography and OCT measurement.

Part of light output from the LCD 39 is reflected by the half-mirror 39A, reflected by the mirror 32, travels through the focusing lens 31 and the dichroic mirror 55, passes through the aperture part of the aperture mirror 21, penetrates the dichroic mirror 46, and refracted by the object lens 22, thereby being projected onto the fundus Ef.

A fixation position of the eye E may be changed by changing the position of the fixation target displayed on the screen of the LCD 39. Examples of fixation positions of the eye E includes a position for acquiring images centered at a macula of the fundus Ef, a position for acquiring images centered at an optic papilla, a position for acquiring images centered at fundus center between the macula and the optic papilla, etc. as in conventional retinal cameras, for example. Moreover, display positions of fixation targets may be arbitrarily changed.

As with conventional retinal cameras, the retinal camera unit 2 is provided with an alignment optical system 50 and a focus optical system 60. The alignment optical system 50 generates a target (alignment target) for position matching (alignment) of the optical system with respect to the eye E. The focus optical system 60 generates a target (split target) for focusing on the eye E.

Light output from the LED 51 in the alignment optical system 50 (alignment light) travels through diaphragms 52 and 53 and a relay lens 54, is reflected by the dichroic mirror 55, passes through the aperture part of the aperture mirror 21, penetrates the dichroic mirror 46, and is projected onto the cornea of the eye E by the object lens 22.

Cornea reflection light of the alignment light travels through the object lens 22, the dichroic mirror 46 and the aperture part, and part of the cornea reflection light penetrates the dichroic mirror 55, passes through the focusing lens 31, is reflected by the mirror 32, penetrates the half-mirror 39A, is reflected by the dichroic mirror 33, and is projected onto the light receiving surface of the CCD image sensor 35 by the condenser lens 34. An image captured by the CCD image sensor 35 (alignment target) is displayed on the display device 3 together with the observation image. A user carries out a similar operation to conventional retinal cameras to conduct alignment. Instead, alignment may be performed in such a way that an arithmetic and control unit 200 analyzes the position of the alignment target to move the optical system (automatic alignment). It should be noted that automatic alignment may be performed using anterior eye cameras 300 (described later) in the present embodiment; therefore, automatic alignment using alignment target is not a necessary function. However, configurations may be adopted in which automatic alignment using alignment target is executed when automatic alignment using the anterior eye cameras 300 fails or in which automatic alignment using the anterior eye cameras 300 and automatic alignment using alignment target are selectively used.

In order to conduct focusing, a reflection surface of a reflection rod 67 is slantingly arranged in the optical path of the illumination optical system 10. Light output from an LED 61 in the focus optical system 60 (focusing light) passes through a relay lens 62, is split into two light fluxes by a split target plate 63, passes through a two-hole diaphragm 64, is reflected by a mirror 65, once forms an image on the reflection surface of the reflection rod 67 by a condenser lens 66 and is reflected by the reflection surface. Further, the focusing light travels through the relay lens 20, is reflected by the aperture mirror 21, penetrates the dichroic mirror 46, and is refracted by the object lens 22, thereby being projected onto the fundus Ef.

The fundus reflection light of the focusing light passes through the same route as the cornea reflection light of the alignment light and is detected by the CCD image sensor 35. An image captured by the CCD image sensor 35 (split target) is displayed on the display device 3 together with an observation image. The arithmetic and control unit 200, as in the conventional case, analyzes the position of the split target and moves the focusing lens 31 and the focus optical system 60 for focusing (automatic focusing). Further, focusing may be performed manually while obeserving the split target.

The dichroic mirror 46 splits the optical path for OCT measurement from the optical path for fundus photography. The dichroic mirror 46 reflects light of wavelength band for OCT measurement and transmits light for fundus photography. The optical path for OCT measurement is provided with a collimator lens unit 40, an optical-path-length changing part 41, a galvano scanner 42, a focusing lens 43, a mirror 44 and a relay lens 45 in order from the OCT unit 100 side.

The optical-path-length changing part 41 is configured to be movable along the direction indicated an arrow shown in FIG. 1, thereby changing the optical path length of measurement light LS. This change in the optical path length is used for correction of the optical path length in accordance with the axial length of the eye E, adjustment of the state of interference, change of sites (fundus Ef, anterior eye part Ea, etc.) measured by OCT, and so on. The optical-path-length changing part 41 is configured to include a corner cube and a mechanism for moving the corner cube, for example. The optical-path-length changing part 41 is used for changing optical path length difference between the optical path of the measurement light LS (measurement optical path) and the optical path of the reference light LR (reference optical path). Further, the length of the measurement optical path may also be changed by moving the whole optical system in the front-rear direction (z-direction) by means of the optical system driver 2A in the present embodiment.

In the present embodiment, the optical path length difference is changed by varying the length of measurement optical path (measurement optical path length); however configurations for changing the optical path length difference are not limited to this. For example, the optical path length difference may be changed by providing a configuration for varying the length of reference optical path (reference optical path length). Moreover, it is possible to provide both of a configuration for changing measurement optical path length and a configuration for changing reference optical path length. Configurations for changing measurement optical path length are not limited to the optical-path-length changing part 41 in the present embodiment and an arbitrary configuration capable of realizing the concerned function may be employed. Similarly, configurations for changing reference optical path length may be arbitrary.

Further, configurations for changing optical path length are not limited to those changing length of an optical path in the real space. For example, arbitrary configurations for changing optical distance of an optical path may be applied such as configurations capable of arranging a member of material having a certain refractive index in at least part of the optical path or configurations capable of changing a refractive index of a member etc. arranged in the optical path, and the like.

Further, means for changing optical path length may be a unit (attachment) that can be attached to the ophthalmologic apparatus 1. For example, it is possible to apply a configuration in which an attachment for anterior-eye-part photography is attached to an ophthalmologic apparatus capable of performing OCT measurement of a fundus or a configuration in which an attachment for fundus photography is attached to an ophthalmologic apparatus capable of performing OCT measurement of an anterior eye part. Such an attachment is arranged between the objective lens 22 and the eye E, for example. Here, the attachment may be arranged at a location away from photographing fields of the anterior eye cameras 300.

The galvano scanner 42 changes travelling direction of light (measurement light LS) travelling along the optical path for OCT measurement. Thereby, the eye E may be scanned by the measurement light LS. The galvano scanner 42 is configured to include, for example, a galvano mirror that deflects the measurement light LS in the x-direction, a galvano mirror that deflects it in the y-direction, and a mechanism that independently drives these. Accordingly, the measurement light LS may be scanned in any direction on the xy-plane.

The retinal camera unit 2 is provided with the anterior eye cameras 300. The anterior eye cameras 300 photograph the anterior eye part Ea from different directions substantially simultaneously. In the present embodiment, two cameras are provided on the surface of the retinal camera unit 2 of the subject side (refer to the anterior eye cameras 300A and 300B shown in FIG. 4A). Moreover, the anterior eye cameras 300A and 300B are provided at positions away from the optical paths of the illumination optical system 10 and the imaging optical system 30 as indicated in FIGS. 1 and 4A. In other words, the anterior eye cameras 300A and 300B are arranged non-coaxially with respect to the illumination optical system 10 and the imaging optical system 30. Hereinafter, the two anterior eye cameras 300A and 300B may be collectively represented by a symbol 300.

In the present embodiment, two anterior eye cameras 300A and 300B are provided; however, the number of anterior eye cameras in an embodiment may be any number of two or more (note that an anterior eye camera is not necessarily provided in the case of using the alignment target). However, taking the arithmetic process (mentioned later) into consideration, it is sufficient to provide a configuration that is capable of photographing an anterior eye part from two different directions substantially simultaneously. Moreover, the anterior eye cameras 300 are separately provided from the illumination optical system 10 and imaging optical system 30 in the present embodiment; however, similar anterior-eye-part photography may be performed using at least the imaging optical system 30. That is, one of two or more anterior eye cameras may be a configuration including the imaging optical system 30. In any case, it is sufficient that the present embodiment is capable of photo-graphing an anterior eye part from two (or more) different directions substantially simultaneously.

It should be noted that "substantially simultaneous" means that a time lag of photographing timings by a degree of being able to ignore eye movements when photographing by means of two or more anterior eye cameras is allowed. Accordingly, it becomes possible for the two or more anterior eye cameras to acquire images in which the eye E are depicted at substantially the same position (direction).

Photography by means of the two or more anterior eye cameras may be moving-image photography or still image photography. In the case of moving-image photography, the abovementioned substantially simultaneous photography of anterior eye part may be realized by controlling so as to match timings of commencement of photography or controlling frame rates or timings of capturing frames. Further, a configuration may be employed so as to associate signals substantially simultaneously input from the two or more anterior eye cameras into a controller 210 (described below) with each other. On the other hand, in the case of still image photography, the purpose may be realized by controlling so as to match timings of photography.

[OCT Unit]

Figure 2:
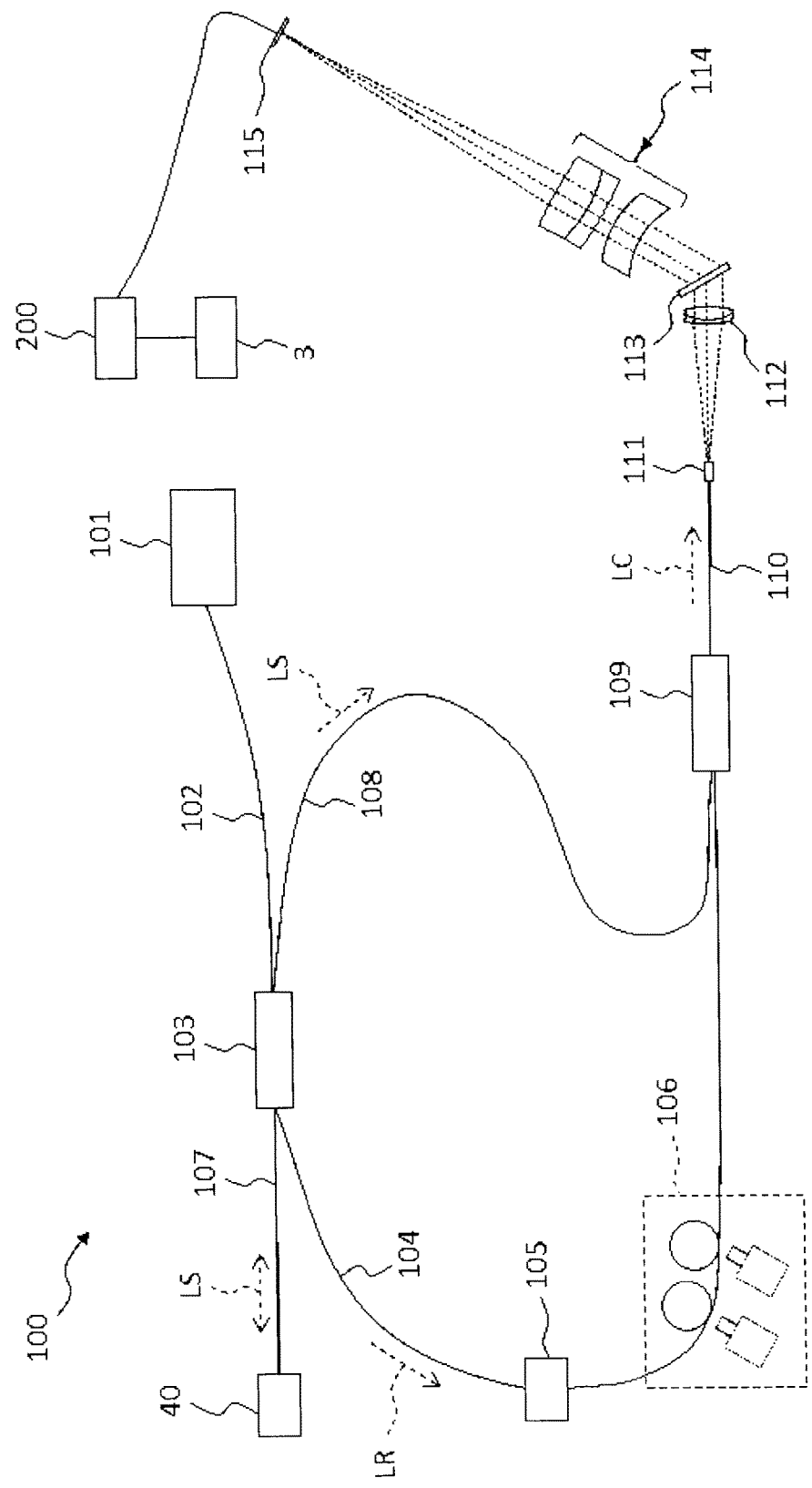
FIG. 2 is a schematic diagram showing an example of the configuration of an ophthalmologic apparatus according to an embodiment.

A configuration example of the OCT unit 100 is described with reference to FIG. 2. The OCT unit 100 is provided with an optical system for acquiring an OCT image of the eye E. The optical system has a similar configuration to a conventional Fourier-domain-type OCT apparatus. That is to say, the optical system is configured to split light (low-coherence light) from a light source into reference light and measurement light, generate interference light by interfering returned light of the measurement light from the eye E and the reference light propagated through a reference optical path, and detect spectral components of the interference light. The result of detection (detection signal) is transmitted to the arithmetic and control unit 200.

It should be noted that, in the case of swept source type OCT apparatus, a wavelength sweeping light source (swept source) is provided instead of a low-coherence light source while an optical element for spectrally decomposing interference light is not provided. Generally, regarding the configuration of the OCT unit 100, known technologies may be applied according to the type of OCT.

The light source unit 101 outputs broadband, low-coherence light L0. The low-coherence light L0 includes near-infrared wavelength bands (approximately 800 nm to 900 nm) and has temporal coherence length of around several tens of micrometers, for example. It should be noted that longer wavelength bands, such as near-infrared light with central wavelength of around 1040 to 1060 nm, may be used as the low-coherence light L0.

The light source unit 101 includes light emitting device such as an SLD (super luminescent diode), LED, SOA (Semiconductor Optical Amplifier) and the like.

The low coherence light L0 output from the light source unit 101 is guided to a fiber coupler 103 through an optical fiber 102 and split into measurement light LS and reference light LR.

The reference light LR is guided through an optical fiber 104 and arrives at an optical attenuator (attenuator) 105. The optical attenuator 105 automatically adjusts light amount of the reference light LR guided through the optical fiber 104 under the control of the arithmetic and control unit 200 by means of known technologies. The reference light LR with the light amount having adjusted by the optical attenuator 105 is guided through the optical fiber 104 and arrives at a polarization adjuster (polarization controller) 106. The polarization adjuster 106 is a device that adjusts polarization state of the reference light LR guided in the optical fiber 104 by applying external stress to the optical fiber 104 of a loop shape. It should be noted that configurations of the polarization adjuster 106 are not limited to this and any known technologies may be employed. The reference light LR with polarization state adjusted by the polarization adjuster 106 arrives at a fiber coupler 109.

The measurement light LS generated by the fiber coupler 103 is guided through an optical fiber 107 and becomes a parallel light flux by the collimator lens unit 40. Further, the measurement light LS arrives at the dichroic mirror 46 via the optical-path-length changing part 41, the galvano scanner 42, the focusing lens 43, the mirror 44 and the relay lens 45. Subsequently, the measurement light LS is reflected by the dichroic mirror 46, refracted by the objective lens 22, and projected onto the eye E. The measurement light LS is scattered and reflected at various depth positions of the eye E. Back-scattered light (returned light) of the measurement light LS from the eye E reversely advances along the same path as the outward path and is guided to the fiber coupler 103, arriving at the fiber coupler 109 via the optical fiber 108.

The fiber coupler 109 causes the back-scattered light of the measurement light LS and the reference light LR having passed through the optical fiber 104 to interfere with each other. Interference light LC thus generated is guided by an optical fiber 110 and output from an exit end 111. Further, the interference light LC is converted to a parallel light flux by a collimator lens 112, spectrally divided (spectrally decomposed) by a diffraction grating 113, converged by the convergence lens 114, and projected onto a light receiving surface of a CCD image sensor 115. It should be noted that although the diffraction grating 113 shown in FIG. 2 is of transmission type, a spectrally decomposing element of any other type may be employed such as a diffraction grating of reflection type.

The CCD image sensor 115 is for example a line sensor, and detects the respective spectral components of the spectrally decomposed interference light LC and converts them into electric charges. The CCD image sensor 115 accumulates these electric charges to generate a detection signal and transmits the signal to the arithmetic and control unit 200.

Although a Michelson-type interferometer is employed in this embodiment, it is also possible to adopt any type of interferometer such as Mach-Zehnder-type as necessary. Instead of a CCD image sensor, other types of image sensors such as a CMOS (Complementary Metal Oxide Semiconductor) image sensor can be used.

[Arithmetic and Control Unit]

A configuration of the arithmetic and control unit 200 is described. The arithmetic and control unit 200 analyzes the detection signals input from the CCD image sensor 115 to form an OCT image of the eye E. An arithmetic processing for this is the same as that of a conventional Fourier-domain-type OCT apparatus.

Further, the arithmetic and control unit 200 controls each part of the retinal camera unit 2, the display device 3 and the OCT unit 100. For example, the arithmetic and control unit 200 controls the display device 3 to display an OCT image of the eye E.

Moreover, as control of the retinal camera unit 2, the arithmetic and control unit 200 executes: control of actions of the observation light source 11, the imaging light source 15 and the LED's 51 and 61; control of action of the LCD 39; control of movements of the focusing lenses 31 and 43; control of movement of the reflection rod 67; control of movement of the focus optical system 60; control of movement of the optical-path-length changing part 41; control of action of the galvano scanner 42; control of actions of the anterior eye cameras 300; and so on.

Further, as control of the OCT unit 100, the arithmetic and control unit 200 executes: control of action of the light source unit 101; control of action of the optical attenuator 105; control of action of the polarization adjuster 106; control of action of the CCD image sensor 115; and so on.

The arithmetic and control unit 200 includes a microprocessor, a RAM, a ROM, a hard disk drive, a communication interface, and so on, as in conventional computers. The storage device such as a hard disk drive stores computer programs for controlling the ophthalmologic apparatus 1. The arithmetic and control unit 200 may be provided with various kinds of circuit boards, such as a circuit board for forming OCT images. Moreover, the arithmetic and control unit 200 may be provided with operation devices (input devices) such as a keyboard and a mouse, and/or display devices such as an LCD.

The retinal camera unit 2, the display device 3, the OCT unit 100 and the arithmetic and control unit 200 may be integrally configured (that is, within a single case), or configured in two or more separated cases.

[Control System]

Figure 3:
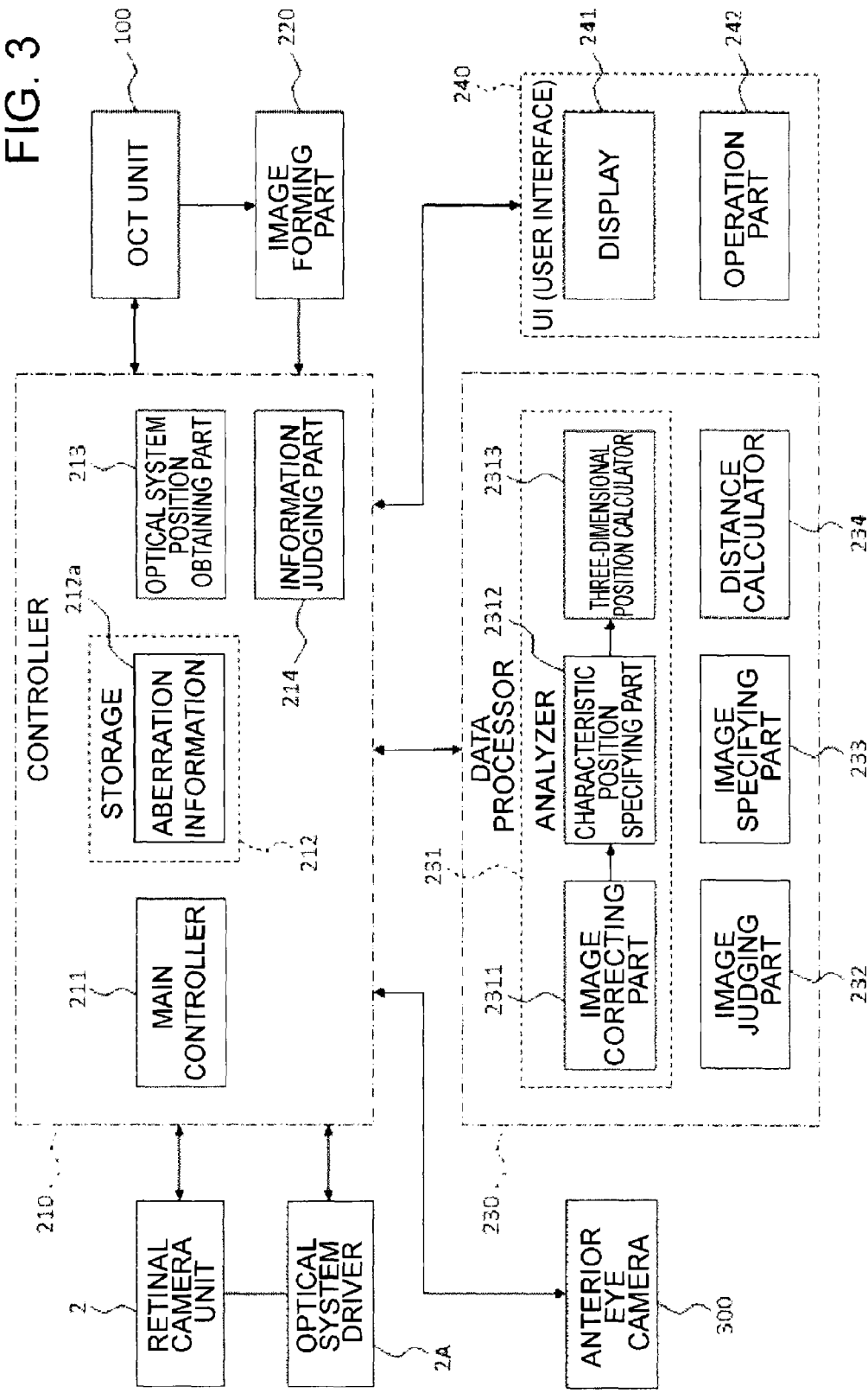
FIG. 3 is a schematic diagram showing an example of the configuration of an ophthalmologic apparatus according to an embodiment.

A configuration of a control system of the ophthalmologic apparatus 1 is described with reference to FIG. 3.

(Controller)

The controller 210 is a center of the control system of the ophthalmologic apparatus 1. The controller 210 includes the aforementioned microprocessor, RAM, ROM, hard disk drive, communication interface, etc., for example. The controller 210 is provided with a main controller 211, a storage 212, an optical system position obtaining part 213 and an information judging part 214.

(Main Controller)

The main controller 211 carries out various kinds of controls described above. The movement control of the focusing lens 31 is for controlling a focus driver (not illustrated) to move the focusing lens 31 in the optical axis direction. Thereby, focus position of the imaging optical system 30 is changed. Moreover, control of the motion of the focusing lens 43 is to moving the focusing lens 43 in the optical axis direction by controlling a focus driver (not illustrated). Thereby, focus position of the measurement light LS is changed.

The main controller 211 is capable of controlling the optical system driver 2A to move the optical system provided in the retinal camera unit 2 three-dimensionally. This control is carried out in automatic alignment and tracking. Here, tracking is an action of moving the optical system of the apparatus in accordance with the eye movement of the eye E. Tracking is performed at the stage after alignment (focusing is also performed in advance if necessary), for example. Tracking is a function causing the position of the optical system of the apparatus to follow the eye movement, thereby maintaining a suitable positional relationship in which alignment (and focusing) is matched.

The optical system driver 2A of the present embodiment moves the optical system installed in the retinal camera unit 2; however, a configuration is possible in which the optical system installed in the retinal camera unit 2 and the optical system installed in the OCT unit 100 are moved by means of the optical system driver 2A. The optical system driver 2A is an example of a "moving mechanism".

The anterior eye cameras 300 of the present embodiment are provided on the case of the retinal camera unit 2, and so the anterior eye cameras 300 can be moved by controlling the optical system driver 2A (camera moving part). Moreover, it is possible to provide a camera moving part capable of independently moving the two or more anterior eye cameras 300. Specifically, the camera moving part may include driving mechanisms (actuator, power transmission mechanism, etc.) provided for each anterior eye camera 300. Further, the camera moving part may be configured to move two or more anterior eye cameras 300 by transmitting power generated by a single actuator by means of the power transmission mechanism provided for each anterior eye camera 300.

The main controller 211 executes processing for writing data into the storage 212 and processing for reading out data from the storage 212.

(Storage)

The storage 212 stores various kinds of data. Examples of the data stored in the storage 212 include image data of OCT images, image data of fundus images, and eye information, for example. The eye information includes information on a subject such as a patient ID and a name and information on an eye such as identification information of left eye or right eye. Moreover, various kinds of programs and data for operating the ophthalmologic apparatus 1 are stored in the storage 212.

Aberration information 212a is stored in the storage 212 in advance. The aberration information 212a includes information regarding distortion aberration occurred in photograph images due to influence of the optical system installed in each anterior eye camera 300. Here, the optical system installed in the anterior eye camera 300 includes optical elements that occurs distortion aberration such as lenses, for example. It may be said that the aberration information 212a is parameters quantifying deformation of photograph images caused by these optical elements.

An example of a method of generating the aberration information 212a is explained. Taking instrumental errors (difference in distortion aberrations) of the anterior eye cameras 300 into consideration, the following measurements are carried out for each anterior eye camera 300. An operator prepares specific reference points. The reference points are photographed targets used for detecting distortion aberration. The operator performs photography multiple times while changing relative position between the reference points and the anterior eye cameras 300. Accordingly, multiple photograph images of the reference points photographed from different directions may be obtained. The operator uses a computer to analyze the multiple photograph images acquired, thereby generating the aberration information 212a of this anterior eye camera 300. The computer for this analysis may be a data processor 230 or any other computer (computer for inspection before shipping products, computer for maintenance, etc.).

The analysis for generating the aberration information 212a includes the following procedures, for example:

an extraction procedure for extracting image regions corresponding to the reference points in each photograph image;

a distribution state calculating procedure for calculating distribution state (coordinates) of the image regions corresponding to the reference points in each photograph image;

a distortion aberration calculating procedure for calculating a parameter indicating distortion aberration based on the obtained distribution state; and correction factor calculating procedure for calculating a factor for correcting the distortion aberration based on the obtained parameter.

Examples of the parameter related to distortion aberration given to an image by the optical system include principal distance, position of a principal point (vertically and horizontally), distortion of a lens (radiation direction and tangential direction), etc. The aberration information 212a is created as information (such as table information) that associates identification information of each anterior eye camera 300 with correction factor corresponding thereto. The aberration information 212a thus generated is stored in the storage 212 by the main controller 211. Generation of such aberration information 212a and aberration correction based on this are referred to as camera calibration etc.

(Optical System Position Obtaining Part)

The optical system position obtaining part 213 obtains current position of the optical system installed in the ophthalmologic apparatus 1. The optical system is used for optically examining the eye E. The optical system in the ophthalmologic apparatus 1 of the present embodiment (combined apparatus of retinal camera and OCT apparatus) is an optical system for acquiring images of an eye.

The optical system position obtaining part 213 receives information presenting content of movement control of the optical system driver 2A by means of the main controller 211 and obtains the current position of the optical system moved by the optical system driver 2A, for example. A specific example of this processing is explained. The main controller 211 controls the optical system driver 2A at a predetermined timing (when starting up the apparatus, when inputting patient information, etc.) to move the optical system to a predetermined initial position. Thereafter, the main controller 211 stores control content each time the optical system driver 2A is controlled. Thereby, a history of the control contents is obtained. The optical system position obtaining part 213 refers to this history to obtain the control contents to date and determines the current position of the optical system based on these control contents.

Alternatively, each time the main controller 211 controls the optical system driver 2A, the control content thereof may be transmitted to the optical system position obtaining part 213, and the current position of the optical system may be determined each time the optical system position obtaining part 213 receives the control content.

As another configuration example, a position sensor detecting the position of the optical system may be provided with the optical system position obtaining part 213.

When the current position of the optical system is obtained by the optical system position obtaining part 213 as stated above, the main controller 211 may control the optical system driver 2A to move the optical system based on the obtained current position and three-dimensional position of the eye E obtained by an analyzer 231 (mentioned later). Specifically, the main controller 211 recognizes the current position of the optical system from the acquisition result by the optical system position obtaining part 213 and recognizes the three-dimensional position of the eye E from the analysis result by the analyzer 231. Subsequently, in order that the position of the optical system with respect to the three-dimensional position of the eye E becomes a predetermined positional relationship, the main controller 211 changes the position of the optical system from the current position thereof as the starting point. This predetermined positional relationship may be such that positions in the x and y-directions coincide while distance in the z-direction becomes a predetermined working distance. Here, the working distance is a preset value also referred to as working distance, meaning the distance between the eye E and the optical system when performing examinations using the optical system.

(Information Judging Part)

The information judging part 214 judges whether or not information acquired by OCT is appropriate for performing OCT. The information acquired by OCT may be detection signals from the CCD image sensor 115 of the OCT unit 100 or information obtained by executing a prescribed processing on the detection signals. Examples of the latter include the following information: a cross sectional image (A-scan image, two-dimensional cross sectional image) formed by an image forming part 220 based on the detection signals; information obtained in the halfway stage of this cross sectional image formation; information (image etc.) formed by the data processor 230 based on one or more cross sectional images formed by an image forming part 220; information obtained by executing processing other than these on the detection signals.

An example of judgment processing based on detection signals from the CCD image sensor 115 is explained. The information judging part 214 analyzes detection signals to derive information indicating a characteristic thereof (characteristic information), and judges whether or not this characteristic information is appropriate for carrying out OCT. Types of the characteristic information may be determined in advance based on influence on the measurement light LS (that is, influence on the interference light LC) from factors that disturb light in an eye.

Intensity (amplitude etc.) is an example of the characteristic information. For example, when the measurement light LS passes through an opaque portion in the eye E, the intensity of the measurement light LS decreases, thereby the intensity of the interference light LC decreases. The information judging part 214 derives the intensity of the detection signal obtained by detecting the interference light LC, and compares this intensity with a threshold. When the intensity is equal to or less than the threshold, the information judging part 214 judges this detection signal is not appropriate. This threshold is defined in advance, for example, based on the intensity of light output from the light source unit 101. The threshold may be defined by taking account of various factors such as light splitting ratio of the fiber coupler 103, light attenuation amounts by optical elements, standard attenuation amount of light that passes through a healthy eye. Amount of noises and SN ratio are examples of the characteristic information other than signal intensity.

Even when taking account of information obtained in the halfway stage of cross sectional image formation or information obtained by executing processing other than image formation on the detection signal, similar processing to the case of taking account of detection signals may be applied. The same applies to the case of taking account of information generated by the data processor 230 (for example, information other than images) based on one or more cross sectional images formed by the image forming part 220.

An example of processing executed by the information judging part 214 is explained. This judgment processing relates to processing called Auto-Z. The Auto-Z is a function for depicting an image of the eye E within a prescribed area (target area) in a frame of an OCT image (cross sectional image).

In the Auto-Z, the same location of the eye E is repeatedly scanned. Trajectory of the respective scans is, for example, of linear shape (line scanning). The information judging part 214 analyzes each of cross sectional images successively acquired by the repetitive scanning to specify, in real time, depth position (position in the z-direction (depth direction)) in the frame at which the image of a prescribed tissue (e.g. the surface of the fundus, a layer tissue with high brightness) of the eye E is depicted. Further, the information judging part 214 calculates displacement between the specified depth position and the target area. The main controller 211 adjusts the optical path length difference between the measurement light LS and the reference light LR so as to cancel the calculated displacement, that is, such that the image of the prescribed tissue is depicted in the target area.

Adjustment of the optical path length difference is carried out by controlling the optical-path-length changing part 41 to change the optical path length of the measurement light LS. A configuration of changing the optical path length of the reference light LR (for example, a variable reference mirror (described later)) may be adopted. Moreover, it is possible to apply both of a configuration for changing the optical path length of measurement light and a configuration for changing the optical path length of reference light.

The main controller 211 and the information judging part 214 carry out the abovementioned processing for the respective cross sectional images (or at a predetermined intervals) obtained by the repetitive scanning. When the abovementioned displacement becomes equal to or less than the threshold before a prescribed timing, that is, when the image of the prescribed tissue is depicted within the target area before the prescribed timing, the information judging part 214 judges the Auto-Z succeeds.

In contrast, when the abovementioned displacement does not become equal to or less than the threshold before the prescribed timing, that is, when the image of the prescribed tissue is not depicted within the target area before the prescribed timing, the information judging part 214 judges the Auto-Z is failed. This prescribed timing is set in advance and may be defined as the number of times of comparison between the abovementioned displacement and the threshold or as the elapsed time from the beginning of the Auto-Z.

Details are described below, but the present embodiment performs OCT measurements of two sites of the eye E (a cornea and a retina, for example) to obtain distance between these two sites. In such processing, Auto-Z may be executed as preparation of OCT measurement. This Auto-Z is executed for arranging a prescribed site of the eye E at a prescribed position in a frame.

For example, when axial length is obtained as an intraocular distance, Auto-Z is carried out for arranging surface of a cornea (corneal apex, for example) at a position in a frame corresponding to a coherence gate, and then OCT measurement of a region including the surface of the cornea is performed. Further, Auto-Z is carried out for arranging surface of a retina (center of the retina, for example) at a position in a frame corresponding to a coherence gate, and then OCT measurement of a region including the surface of the retina is performed. Processing according to the present embodiment may be performed regardless of success/failure in such Auto-Z. Here, a coherence gate is a position at which difference between measurement optical path length and reference optical path length is zero.

(Image Forming Part)

The image forming part 220 forms image data of a cross sectional image of the eye E based on detection signals from the CCD image sensor 115. Like conventional spectral-domain-type OCT, this processing includes processing such as noise elimination (noise reduction), filtering and FFT (Fast Fourier Transform), etc. In the case of applying other types of OCT, the image forming part 220 executes known processing in accordance with the type thereof.

The image forming part 220 includes the aforementioned circuit boards, for example. "Image data" and "image" based on this may be identified with each other in this specification.

(Data Processor)

The data processor 230 executes various image processing and analysis on images formed by the image forming part 220. For example, the data processor 230 executes various corrections such as luminance correction and dispersion compensation of images. Moreover, the data processor 230 executes various image processing and analysis on images (fundus images, anterior-eye images, etc.) acquired by the retinal camera unit 2.

The data processor 230 executes known image processing such as interpolation that interpolates pixels between cross sectional images to form three-dimensional image data of the eye E. The three-dimensional image data refers to image data in which positions of pixels are defined by a three-dimensional coordinate system. The three-dimensional image data is, for example, image data composed of three-dimensionally arranged voxels. This image data is referred to as volume data, voxel data, etc. In order to display an image based on volume data, the data processor 230 executes rendering processing (such as volume rendering and MIP (Maximum Intensity Projection)) on this volume data to form image data of a pseudo three-dimensional image taken from a specific view direction. This pseudo three-dimensional image is displayed on a display 241.

It is also possible to form stack data of multiple cross sectional images as three-dimensional image data. Stack data is image data obtained by three-dimensionally arranging multiple cross sectional images obtained along multiple scanning lines based on the positional relation of the scanning lines. That is, stack data is image data obtained by expressing multiple cross sectional images originally defined by individual two-dimensional coordinate systems by one three-dimensional coordinate system (in other words, by embedding into a three-dimensional space).

The data processor 230 may form a cross sectional image at an arbitrary cross section based on three-dimensional image data. This processing is called MPR (Multi-Planar Reconstruction) etc. and includes processing for extracting picture elements (voxels) located at a designated cross section and processing for arranging the extracted picture elements.

The data processor 230 is provided with an analyzer 231, image judging part 232, image specifying part 233 and distance calculator 234.

(Analyzer)

The analyzer 231 analyzes two or more photograph images substantially simultaneously obtained by the two or more anterior eye cameras 300 to acquire three-dimensional position of the eye E. As an example of a configuration for performing this processing, the analyzer 231 is provided with an image correcting part 2311, characteristic position specifying part 2312 and three-dimensional position calculator 2313.

(Image Correcting Part)

The image correcting part 2311 corrects distortion of each photograph image obtained by the anterior eye cameras 300 based on the aberration information 212a stored in the storage 212. This processing may be carried out by, for example, known image processing technology based on correction factors for correcting distortion aberration. When distortion aberration caused in photograph images due to the optical system of the anterior eye cameras 300 is sufficiently small and the like, there is no need to provide the aberration information 212a and the image correcting part 2311.

(Characteristic Position Specifying Part)

The characteristic position specifying part 2312 analyzes each photograph image (whose distortion aberration has been corrected by the image correcting part 2311) to specify the position in the photograph image corresponding to a predetermined characteristic site of the anterior eye part Ea (referred to as characteristic position). The predetermined characteristic site may be center of a pupil or corneal apex of the eye E, for example. Hereinafter, a specific example of processing for specifying the center of the pupil is explained.

First, the characteristic position specifying part 2312 specifies an image region (pupillary region) corresponding to the pupil of the eye E based on distribution of pixel values (luminous values etc.) in a photograph image. Generally, a pupil is represented by lower luminance compared to other sites, so a pupillary region may be specified by searching an image region with low luminance. At this time, the pupillary region may be specified taking the shape of the pupil into consideration. That is, a pupillary region may be specified by searching a substantially circular image region with low luminance.

Next, the characteristic position specifying part 2312 specifies center position of the specified pupillary region. Since a pupil is substantially circular as mentioned above, it is possible to specify contour of the pupillary region, specify center position of this contour (approximate circle or approximate ellipse thereof), and treat this as the center of the pupil. Alternatively, it is possible to derive center of gravity of the pupillary region and treat this center of gravity as the center of the pupil.

It should be noted that even when characteristic position corresponding to other characteristic site is to be specified, the characteristic position may be specified based on pixel-value distribution of a photograph image in the same manner as above.

(Three-Dimensional Position Calculator)

The three-dimensional position calculator 2313 calculates three-dimensional position of the eye E based on the positions of the two or more anterior eye cameras 300 and the characteristic positions in the two or more photograph images specified by the characteristic position specifying part 2312. This processing is explained with reference to FIGS. 5A and 5B.

Figure 5A:
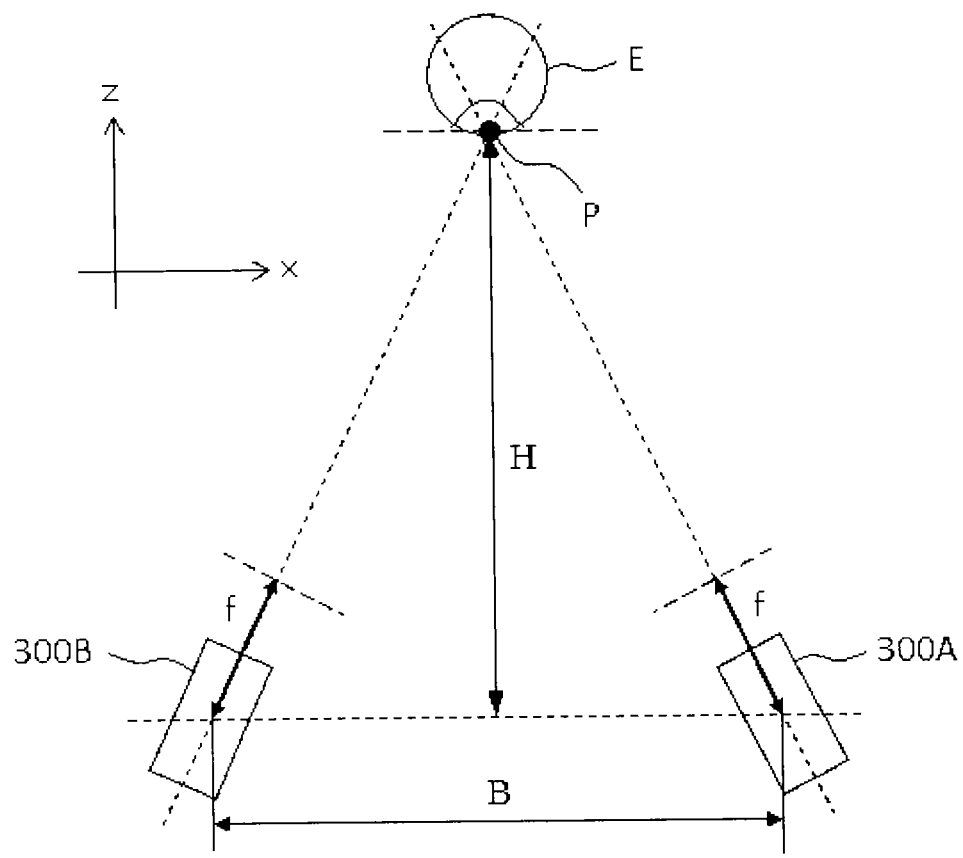
FIG. 5A is a schematic diagram for explaining an operation example of an ophthalmologic apparatus according to an embodiment.
Figure 5B:
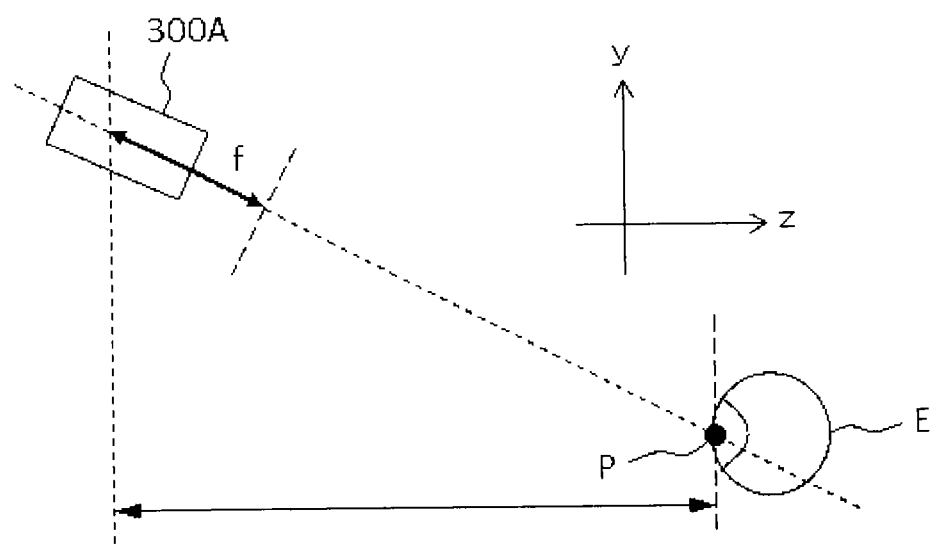
FIG. 5B is a schematic diagram for explaining an operation example of an ophthalmologic apparatus according to an embodiment.

FIG. 5A is a top view illustrating positional relationship between the eye E and the anterior eye cameras 300A and 300B. FIG. 5B is a side view illustrating positional relationship between the eye E and the anterior eye cameras 300A and 300B. Distance between the two anterior eye cameras 300A and 300B (base line length) is represented as "B". Distance between the base line of the two anterior eye cameras 300A and 300B and a characteristic site P of the eye E (photography distance) is represented as "H". Distance between the respective anterior eye cameras 300A and 300B and a screen plane thereof (screen distance) is represented as "f".

In such an arrangement state, resolution of a photograph image acquired by the anterior eye cameras 300A and 300B is expressed by the following formula. Here, $\Delta p$ represents pixel resolution.

$xy$-resolution (planar resolution): $\Delta xy = H \times \Delta p / f$ $z$-resolution (depth resolution): $\Delta z = H \times H \times \Delta p / (B \times f)$ The three-dimensional position calculator 2313 applies known trigonometry, in which the positional relationship indicated in FIG. 5A and FIG. 5B is taken into consideration, to the positions of the two anterior eye cameras 300A and 300B (these are known) and the characteristic positions corresponding to the characteristic site P in the two photograph images, thereby calculating three-dimensional position of the characteristic site P, that is, three-dimensional position of the eye E.

The three-dimensional position of the eye E calculated by the three-dimensional position calculator 2313 is transmitted to the controller 210. Based on this calculation result of the three-dimensional position, the controller 210 controls the optical system driver 2A such that the optical axis of the optical system matches the axis of the eye E and such that the distance of the optical system from the eye E becomes the predetermined working distance.

When the anterior eye cameras 300 acquire moving images of the anterior eye part Ea from different directions simultaneously, tracking of the optical system with respect to movement of the eye E becomes possible by executing the following processing (1) and (2), for example.

(1) The analyzer 231 successively analyzes two or more frames substantially simultaneously obtained by acquiring moving pictures using the two or more anterior eye cameras 300 to successively obtain three-dimensional positions of the eye E.

(2) The controller 210 successively controls the optical system driver 2A based on the three-dimensional positions of the eye E successively obtained by the analyzer 231, thereby causing the position of the optical system to follow movement of the eye E.

The analyzer 231 may derive displacement between the eye E and the optical system based on the three-dimensional position obtained by the three-dimensional position calculator 2313. This processing may be carried out by utilizing the fact that the positions of the anterior eye cameras 300 and the position of the optical system are known. Here, the position of the optical system is a position given in advance, and is an intersecting position of the front surface (surface facing the eye E) of the objective lens 22 and the optical axis of the optical system, for example.

Another example of processing for deriving displacement between the eye E and the optical system is explained. In the present example, the alignment target is projected onto the anterior eye part of the eye E. Further, a moving picture of the anterior eye part onto which the alignment target is being projected is acquired by the retinal camera unit 2. In general, a pair of alignment targets is displayed in each frame of this moving picture. The analyzer 231 calculates objective displacement based on depicted position of the pair of the alignment targets.

This processing is explained more specifically. Once the optical system is positioned in a prescribed examinable position relative to the eye E, a pair of the alignment targets is displayed over a prescribed position of the frame (the center of the frame, for example). The examinable position corresponds to positional relationship between the eye E and the optical system such that, for example, the x-coordinate and the y-coordinate of a prescribed site of the eye E (e.g. the corneal apex, the center of the pupil) and the x-coordinate and the y-coordinate of the optical axis of the optical system are substantially equal, and such that the distance between the eye E and the optical system (e.g. the objective lens 22) is substantially equal to the prescribed working distance. Further, gap (first gap) between the displayed positions of the two alignment targets reflects displacement from the working distance in the z-direction, and gap (second gap) of the displayed positions of the alignment targets relative to the prescribed position of the frame reflects displacement from the prescribed site of the eye E in the xy-direction. The analyzer 231 utilizes this relationship to derive the displacement in the z-direction from the first gap and the displacement in the xy-direction from the second gap. Thereby, the three-dimensional displacement between the eye E and the optical system is obtained. Such processing for calculating displacement is carried out in known automatic alignment.

(Image Judging Part)

The image judging part 232 analyzes a photograph image(s) obtained by at least one of the two or more anterior eye cameras 300 to judge whether or not image of the anterior eye part Ea is within a predetermined area in the photograph image(s).

This predetermined area is set in advance within the photographed region of the anterior eye camera 300 and set as a region including the center of this photographing region, for example. Here, extent of the predetermined area may be changed in accordance with the photographing conditions of the anterior eye camera 300 (position, photographic magnification, etc. of the anterior eye cameras 300). Moreover, the extent of the predetermined area may be determined in accordance with a setting of a characteristic point described later. Further, the predetermined area may be set such that it corresponds to the position of the supporter 440 (jaw holder, forehead rest, etc.; refer to FIGS. 4A and 4B) supporting the face of the subject or the vicinity position thereof.

A specific example of processing executed by the image judging part 232 is explained. First, the image judging part 232 specifies an image region corresponding to a predetermined characteristic point of the anterior eye part Ea from a photograph image. This characteristic point may be center of the pupil, contour of the pupil, center of the iris, contour of the iris, corneal apex, etc. Processing for specifying the image region corresponding to the characteristic point is carried out similarly to the processing carried out by the characteristic position specifying part 2312, for example. When the characteristic point and the characteristic site are the same, the specification result by the characteristic position specifying part 2312 may be utilized for the processing executed by the image judging part 232.

Next, the image judging part 232 judges whether or not the specified characteristic point is within the predetermined area of the photograph image (the frame thereof). This processing may be carried out by comparing the coordinates corresponding to the predetermined area and the coordinates of the characteristic point.

The image judging part 232 transmits this determination result to the controller 210. When it is determined that the image of the anterior eye part Ea is not included in the predetermined area, the controller 210 controls the optical system driver 2A (camera moving part) to move the anterior eye cameras 300 in a direction away from the supporter 440 (that is, the face of the subject) and/or a direction outwards of the supporter 440. The direction away from the supporter 440 is the −z-direction in the coordinate system indicated in FIG. 1 etc. Moreover, the direction outwards of the supporter 440 is the direction in which the anterior eye cameras 300 moves away from the optical axis of the optical system. The direction away from the optical system may be defined horizontally (±x direction) and/or vertically (±y direction). That is, the direction away from the optical system may be defined in any direction in the xy-plane.

Moreover, moving direction and/or moving distance of the anterior eye camera 300 may be set based on positional relationship between the anterior eye camera 300 and the supporter 440 before movement, for example. Moreover, it is possible to perform determination processing by the image judging part 232 and moving processing of the anterior eye camera 300 alternately, thereby executing control so as to move the anterior eye camera 300 to a suitable position. Moreover, it is possible to determine moving direction and/or moving distance of the anterior eye camera 300 in accordance with distance (number of pixels) between the image region corresponding to the characteristic point and the predetermined area. Moreover, it is possible to determine moving direction and/or moving distance of the anterior eye camera 300 in accordance with distance between the image region corresponding to the characteristic point and a predetermined position (center position thereof, for example) in the predetermined area.

Other operation examples based on determination result by the image judging part 232 are explained. When it is determined that the image of the anterior eye part Ea is not included in the predetermined area, the controller 210 controls an output part to output predetermined warning information. This output part may be the display 241, an audio output part (not illustrated), etc. When using the display 241 as the output part, the controller 210 controls the display 241 to display a warning message including predetermined text string information, image information, pop-up window, etc. When the audio output part is used as the output part, the controller 210 controls the audio output part to output predetermined voice information, warning sound, etc.

From such warning information, the user recognizes that the image of the anterior eye part Ea is not included in the predetermined area. Subsequently, the user can use an operation part 242 to move the anterior eye camera 300 three-dimensionally. It should be noted that the controller 210 may output information (movement information) indicating moving direction and/or moving distance of the anterior eye camera 300 together with warning information. This movement information is generated based on positional relationship between an image region corresponding to the characteristic point obtained by the image judging part 232 and the predetermined area, for example. It is possible that determination processing is carried out again by the image judging part 232 once manual movement by the user is completed.

(Image Specifying Part)

The image specifying part 233 operates when the anterior eye cameras 300 acquire time-series images, for example. A time-series image includes multiple still images (frames) arranged in time series (in a time axis). A time-series image may be a moving image. Here, a moving image means a succession of still images acquired synchronously with a time axis (that is, at constant time intervals) and represents movement of an object. A time-series image is not limited to a moving image and time intervals between frames may not need to be constant, for example.

The image specifying part 233 compares still images successively acquired as a time-series image with a preset reference image (first image) to specify a still image (second image) substantially same as this reference image. This comparison processing includes arbitrary image processing for judging identity (degree of similarity) of two images. This image processing may include any of image correlation, extraction of characteristic points, image subtraction, affine transformation, etc., for example.

In this comparison processing, first and second images may be images acquired by each of the two anterior eye cameras 300A and 300B. In this case, the image specifying part 233 compares first and second images acquired by the anterior eye cameras 300A and compares first and second images acquired by the anterior eye cameras 300B. Alternatively, any of first and second images may be a composite image (such as a stereo image) of two images acquired by the two anterior eye cameras 300A and 300B substantially simultaneously. In this case, the image specifying part 233 compares a composite image corresponding to a first image and a second image corresponding to a second image.

"Substantially the same" is intended to permit difference of two images to a preset extent. For example, the image specifying part 233 stores permissible range of image correlation value in advance and judges whether or not a correlation value obtained by image correlation in the above comparison processing is included in the permissible range. When it is included in the permissible range, it is judged that two images compared are substantially the same. A still image that has been judged to be substantially the same corresponds to the second image described above. The permissible range may be set empirically or theoretically by taking the purpose that intraocular distance are obtained into consideration (the same applies hereinafter).

Another example is explained. The image specifying part 233 previously stores permissible range of disparity of positional relationship (distance, relative position, etc.) of two or more characteristic points. A characteristic point is a position in an image corresponding to an arbitrary site of an eye (such as center or edge of a pupil). Further, the image specifying part 233 executes characteristic point extraction to obtain positional relationship of two or more characteristic points in a first image (reference image) and positional relationship of two or more characteristic points in a still image included in a time-series image. Then, the image specifying part 233 calculates an index indicating disparity between these two positional relationships (difference, ratio, etc.) and judges whether or not this index is included in the permissible range. When it is included in the permissible range, it is judged that the two images compared are substantially the same. The still image that has been judged to be substantially the same corresponds to the second image described above.

Further example is explained. The image specifying part 233 previously stores permissible range of information relating pixels in a subtraction image (difference image) (such as the number of pixels or pixel value). The image specifying part 233 generates a subtraction image between a first image (reference image) and a still image included in a time-series image. Here, position matching (affine transformation) of two images may be performed so as to match two or more characteristic points. Further, the image specifying part 233 obtains information relating pixels in the generated subtraction image and judges whether or not the obtained information is included in the permissible range. When it is included in the permissible range, it is judged that the two images compared are substantially the same. The still image that has been judged to be substantially the same corresponds to the second image described above.

(Distance Calculator)

Based on information acquired by first OCT measurement performed together with acquisition of the reference image and information acquired by second OCT measurement performed together with acquisition of the image substantially the same as the reference image (the second image described above), the distance calculator 234 calculates distance between a first site included in scanning area of the first OCT measurement and a second site included in scanning area of the second OCT measurement.

Here, information obtained by OCT measurement includes the optical path length of the measurement optical path or reference optical path, and in particular, includes information relating the measurement optical path (such as position of the optical-path-length changing part 41, content of control relating movement of the optical-path-length changing part 41) in the present embodiment. In the case in which a configuration capable of changing the reference optical path length is adopted, information relating the reference optical path (such as position of a reference mirror, content of control relating movement of the reference mirror) is included.

Content of processing executed by the distance calculator 234 may be modified in accordance with positions of the first and second sites in information acquired by OCT measurement (such as detection signals, OCT images, information generated by processing detection signals or OCT images).

For example, the content of processing may be modified based on displacement of the first site from a coherence gate (first displacement) and displacement of the second site from a coherence gate (second displacement). These displacements may be used for judgment of success/failure in Auto-Z described above, for example.

When both the first and second displacements are within a preset threshold (when Auto-Z is succeeded, for example), that is, when both the first and second sites correspond to coherence gates, the distance calculator 234 calculates difference between measurement optical path length in the first OCT measurement (first optical path length) and measurement optical path length in the second OCT measurement (second optical path length). The calculated value of the difference corresponds to the distance between the first and second sites.

On the other hand, when one or both of the first and second displacements is greater than the preset threshold (when Auto-Z is failed, for example), that is, when at least one of the first and second sites corresponds to a location(s) apart from a coherence gate(s), the distance calculator 234 refers to displacement(s) of the first site and/or second site from the coherence gate(s) in addition to the first and second optical path lengths described above to calculate distance between these sites. As a specific example thereof, the distance calculator 234 may execute the following three-step processing: first processing for calculating difference between the first and second optical path lengths; second processing for calculating displacement between the first and/or second sites and the coherence gate(s); third processing for calculating distance between the first and second sites based on the difference obtained from the first processing and the displacement obtained from the second processing.

In the second processing, amount and direction of displacement are obtained. Displacement amount is calculated based on position of a signal corresponding to a coherence gate and position of a signal corresponding to a target site in a A-scan profile, for example. Alternatively, displacement amount may be calculated based on image position corresponding to a coherence gate and image position corresponding to a target site in an OCT image. Further, displacement direction is calculated based on positional relationship between the first and second sites (known) as well as position of a signal corresponding to a coherence gate and position of a signal corresponding to a target site in a A-scan profile, for example. Alternatively, displacement direction may be calculated based on positional relationship between the first and second sites (known) as well as image position corresponding to a coherence gate and image position corresponding to a target site in an OCT image.

In the third processing, the displacement amount is added to or subtracted from the value of difference obtained by the first processing according to the displacement direction. Specifically, when the displacement direction of the first (or second) site from the coherence gate is on the second-site side (or first-site side), the displacement amount is subtracted from the value of difference. For example, when the displacement direction of the corneal apex (or center of the retina) from the coherence gate is on the retina side (or cornea side), the displacement amount is subtracted from the value of difference.

In contrast, when the displacement direction of the first (or second) site from the coherence gate is on the opposite side to the second site (or the opposite side to the first site), the displacement amount is added to the value of difference. For example, when the displacement direction of the corneal apex (or center of the retina) from the coherence gate is on the opposite side to the retina (or the opposite side to the cornea), the displacement amount is added to the value of difference.

In the present embodiment, first and second OCT measurements are performed at timings at which substantially the same images are acquired by the anterior eye camera 300. In other words, first and second OCT measurements are performed in states in which relative positions between the eye E and the ophthalmologic apparatus 1 are substantially the same. Thus, difference of the relative positions is not taken used in the distance calculation described above. However, accuracy of distance calculation may be improved by taking this difference of the relative positions into account. For this purpose, displacement between a reference image (first image) and a second image is obtained by executing similar image comparison to the image specifying part 233. Here, each of these images is acquired by the two anterior eye cameras 300A and 300B, and so three-dimensional position of the eye E may be obtained at the respective photography timings as described above (refer to the analyzer 231, in particular the three-dimensional position calculator 2313). Consequently, difference of the relative positions obtained from these images represents three-dimensional displacement (in the x-direction, y-direction and z-direction). Displacement in the z-direction is added to or subtracted from the value of distance obtained by the third processing as with the processing that uses displacement direction and displacement amount obtained by the second processing. Displacement in the x-direction and displacement in the y-direction are considered together with the value of distance obtained by the third processing by means of trigonometry.

The data processor 230 functions as above and includes the aforementioned microprocessor, RAM, ROM, hard disk drive, circuit board, etc. for example. Computer programs causing the microprocessor to execute the above functions are previously stored in a storage device such as the hard disk drive.

(User Interface)

A user interface 240 includes the display 241 and the operation part 242. The display 241 includes the aforementioned display device of the arithmetic and control unit 200 and/or the display device 3. The operation part 242 includes the aforementioned operation device of the arithmetic and control unit 200. The operation part 242 may include various buttons or keys provided on the case of the ophthalmologic apparatus 1 or its outside. For example, if the retinal camera unit 2 has a case similar to conventional retinal cameras, a joy stick, operation panel, etc. provided on this case may be included in the operation part 242. The display 241 may include various display devices such as a touch panel provided on the case of the retinal camera unit 2.

The display 241 and the operation part 242 do not need to be configured as separate devices. For example, like a touch panel, a device having both of display function and operation function may be adopted. In such cases, the operation part 242 includes the touch panel and computer programs. The content of operation to the operation part 242 is input to the controller 210 as electric signals. Moreover, operations and information inputs may be performed by means of graphical user interface (GUI) presented on the display 241 and the operation part 242.

[Operations]

Figure 6:
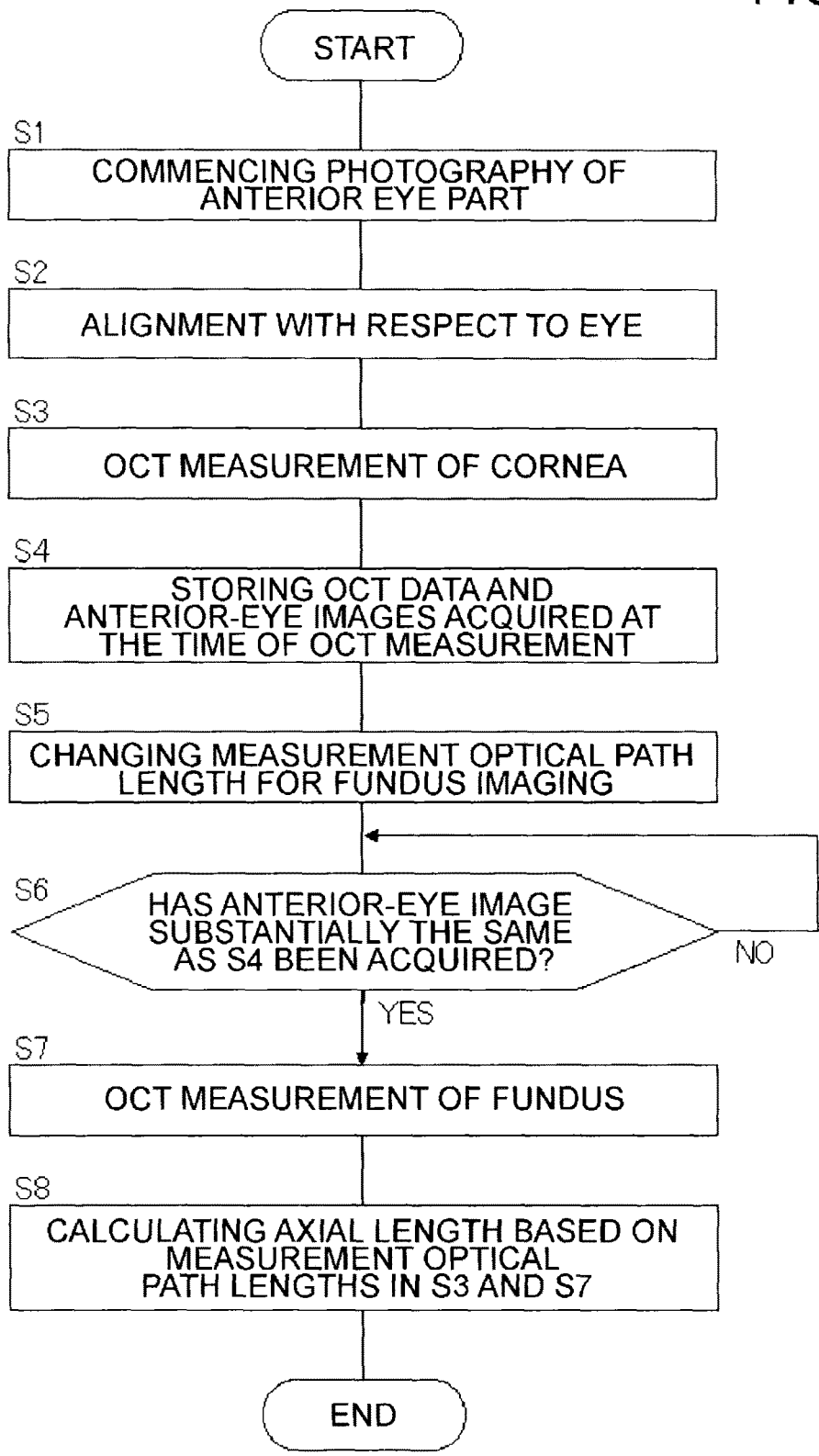
FIG. 6 is a flowchart showing an operation example of an ophthalmologic apparatus according to an embodiment.
Figure 7B:
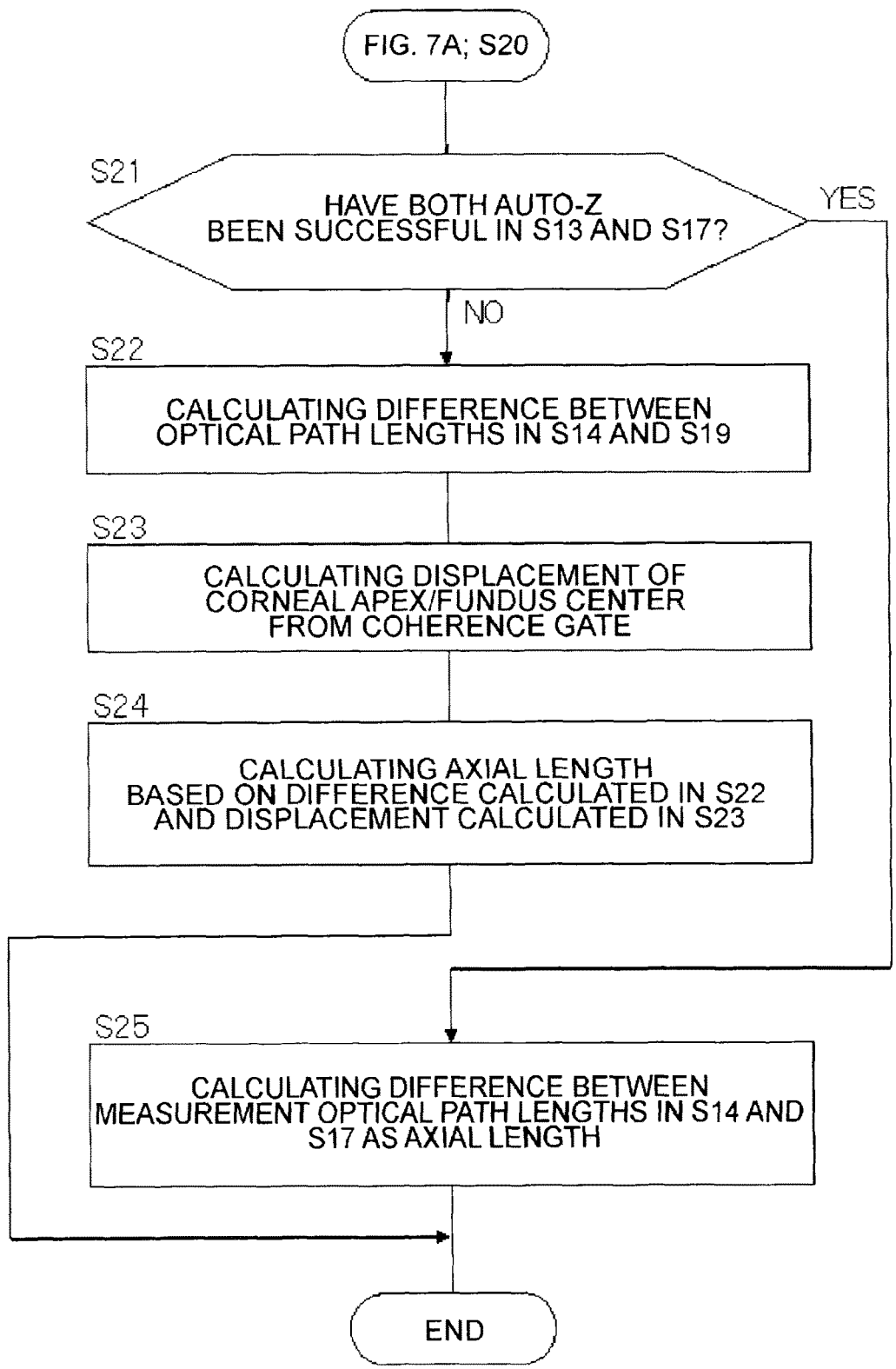
FIG. 7B is a flowchart showing an operation example of an ophthalmologic apparatus according to an embodiment.
Figure 7C:
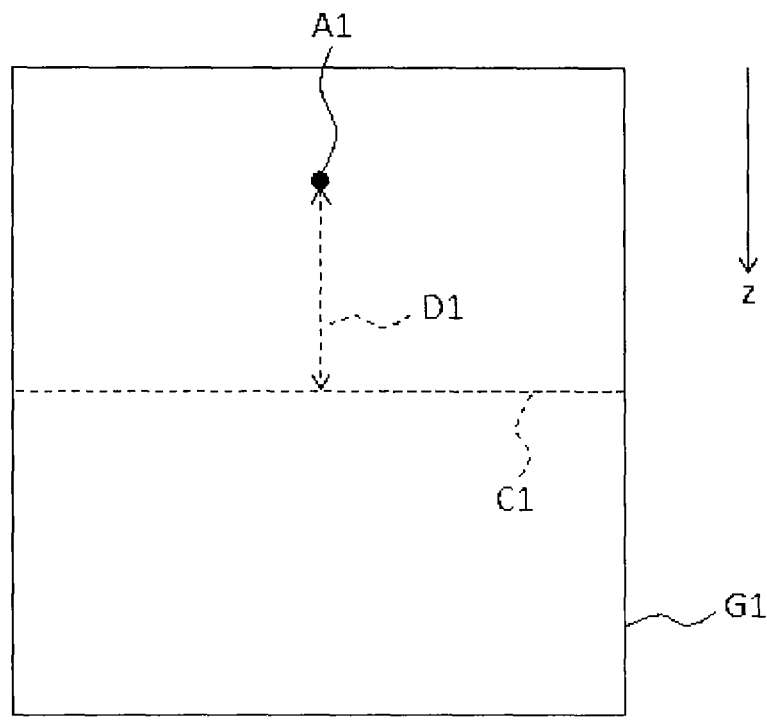
FIG. 7C is a schematic diagram for explaining an operation example of an ophthalmologic apparatus according to an embodiment.
Figure 7D:
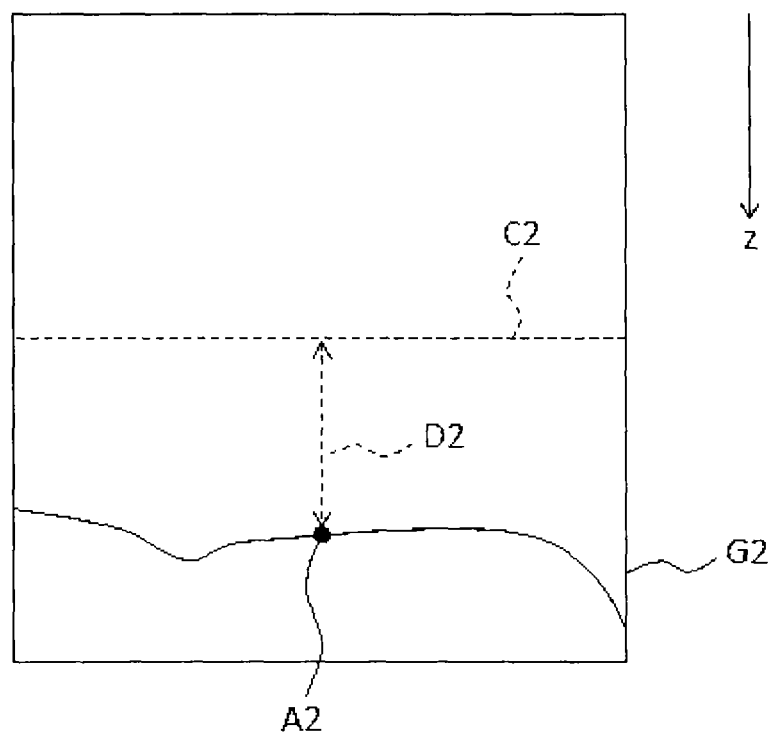
FIG. 7D is a schematic diagram for explaining an operation example of an ophthalmologic apparatus according to an embodiment.
Figure 8:
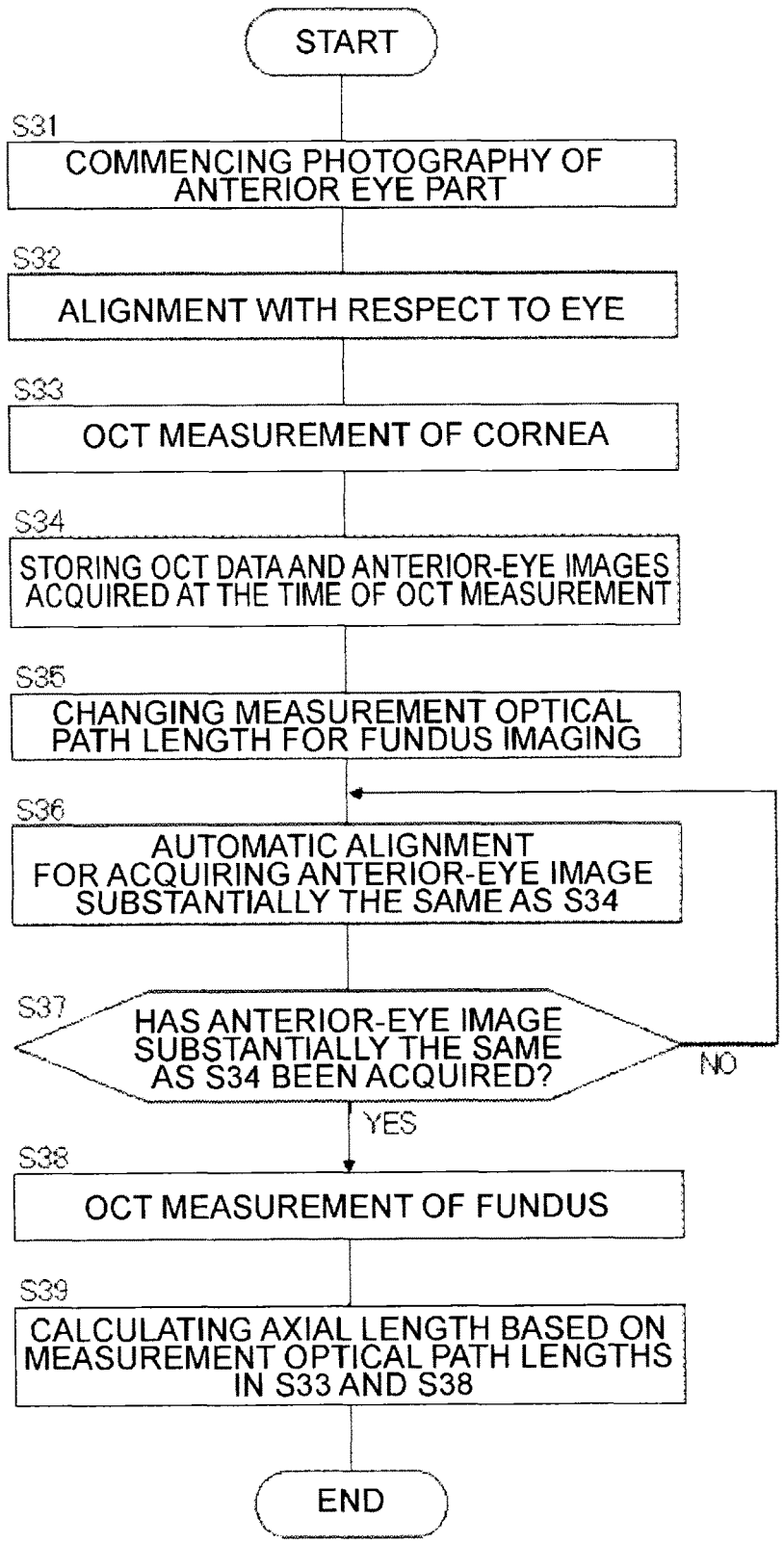
FIG. 8 is a flowchart showing an operation example of an ophthalmologic apparatus according to an embodiment.

Operations of the ophthalmologic apparatus 1 are described. Operation examples of the ophthalmologic apparatus 1 are shown in FIGS. 6 to 8. An operation shown in FIG. 6 illustrates a basic operation of the present embodiment. An operation shown in FIGS. 7A to 7D illustrates an operation example in the case of applying Auto-Z. An operation shown in FIG. 8 illustrates an operation example in the case of applying automatic alignment by means of the abovementioned reference image. Operations according to the present embodiment are not limited to these. For example, any two or more of the three operation examples shown in FIGS. 6 to 8 may be combined.

In the following operation examples, it is assumed that registration of patient and setting of examination conditions have been done already. Patient registration is carried out by inputting patient ID of a concerned subject by means of the user interface 240, for example.

Examination conditions may include various kinds of conditions applied in OCT measurement and/or subsequent processing thereof (scanning pattern, kinds of analysis, etc.). Such conditions may be preset or selected manually or automatically.

Examination conditions may include kinds of intraocular distance to be measured. Kinds of intraocular distance may be identified by any information required to define intraocular distance such as names of intraocular distance (e.g. axial length, lens-retina distance), names of an end(s) of a line segment corresponding to intraocular distance (e.g. cornea (corneal apex), retina (center of retina), posterior capsule of lens (center of posterior capsule of lens), for example. Setting of intraocular distance may include processing for inputting such information.

Some examples of processing for setting a kind of intraocular distance are explained. A first example is described. The controller 210 displays an image of an eye (eye image) on the display 241. Eye images may include any of OCT images, anterior-eye images, fundus images, SLO images and schemata (of anterior eye part, fundus, etc.), for example. Eye images may be images presenting the eye E or other eye. In the case in which an eye image is an image of the eye E, this eye image may be an image acquired in the past (in the past examination, present examination, etc.) or may be an image acquired in real time (observation image, real-time OCT image, etc.). The user used the user interface 240 to designate a desired position in an eye image being displayed. This designating operation is carried out for each of one or more eye images. For example, when axial length is to be designated as kind of intraocular distance, the user designates position of corneal apex in an OCT image of a cornea by click operation or touch operation and designates position of fundus center in an OCT image of a fundus. The controller 210 stores information indicating the designated image positions (coordinate values of pixels, name of sites, etc.) in the storage 212. Intraocular distance specified by the image positions thus designated will be measured in the following processing. The designated image position may be used for any processing such as Auto-Z.

A second example of processing for setting a kind of intraocular distance is explained. The controller 210 displays list information including, as choices, a plurality of information indicating a plurality of kinds of intraocular distance such as names of sites of an eye or names of intraocular distance. An example of the list information may be a list attached by a pull-down menu or check boxes. The user designates a desired choice by using the user interface 240. The controller 210 stores information indicating result of designation of the choice. Intraocular distance will be measured based on the designated choice in the following processing. For instance, the data processor 230 analyzes an OCT image to specify an image region of a site corresponding to the designated choice. As an example, when axial length is to be set as a kind of intraocular distance, the user designates a choice "axial length" or choices "cornea (corneal apex)" and "fundus (fundus center)". Based on the result of designation, the data processor 230 analyzes an OCT image of an anterior eye part to specify an image region corresponding to a corneal apex and analyzes an OCT image of a fundus to specify an image region corresponding to a fundus center.

A third example of processing for setting a kind of intraocular distance is explained. The controller 210 acquires information indicating a kind of intraocular distance such as names of sites of an eye or a name of intraocular distance. This processing is executed by referring to a name of disease recorded in an electronic medical record of a concerned patient, a phase of examination in clinical path, a phase of examination in health screening, etc., for example. Such information is input from an in-hospital server to the ophthalmologic apparatus 1 via a network, for example. The controller 210 stores the acquired information in the storage 212. Intraocular distance will be measured based on the stored information in the following processing. This processing may be the same as the second example.

Preparation described above is carried out prior to respective operations indicated in FIGS. 6 to 8. Processing performed in the preparation stage is not limited to the above ones and may include arbitrary preparatory processing performed in general, for example.

(OPERATION EXAMPLE 1)

The flowchart shown in FIG. 6 is referred to. The present example illustrates an example of basic operation for obtaining intraocular distance.

(S1 : Commencing Photography of Anterior Eye Part)

Once prescribed instruction is input after the preparation described above, the controller 210 controls the anterior eye cameras 300A and 300B to commence photography of the anterior eye part Ea. This photography is moving-image photography to image the anterior eye part Ea. The respective anterior eye cameras 300A and 300B perform moving-image photography at a predetermined frame rate.

Here, the timings of photographing by the anterior eye cameras 300A and 300B may be synchronized by the controller 210. The respective anterior eye cameras 300A and 300B successively transmit acquired frames to the controller 210 in real time. The controller 210 associates frames obtained by both anterior eye cameras 300A and 300B in accordance with the photography timings. That is, the controller 210 associates frames substantially simultaneously acquired by both anterior eye cameras 300A and 300B with each other. This association is carried out, for example, based on the abovementioned synchronous control or based on input timings of frames from the anterior eye cameras 300A and 300B. The controller 210 transmits a pair of the associated frames to the analyzer 231.

The above instruction being a trigger of commencement of photography is input by operation of the user interface 240 performed by the user. Alternatively, the above instruction may be completion of the above preparation.

(S2: Alignment)

Upon receiving commencement of anterior-eye-part photography or upon receiving instruction from the user, the ophthalmologic apparatus 1 starts alignment of the optical system with respect to the eye E. The alignment is performed in order to arrange the optical system at a location (a predetermined relative position with respect to the eye E) for carrying out OCT measurement of the anterior eye part Ea. The alignment is performed based on anterior-eye images acquired by the anterior eye cameras 300A and 300B in real time.

The alignment based on anterior-eye images (frames) acquired by the anterior eye cameras 300A and 300B is executed in the following way, for example. To begin with, the image correcting part 2311 corrects distortion of each frame transmitted from the controller 210 based on the aberration information 212a. A pair of frames whose distortions have been corrected is transmitted to the characteristic position specifying part 2312. The characteristic position specifying part 2312 analyzes each frame transmitted from the image correcting part 2311 to specify a characteristic position in this frame corresponding to the center of the pupil of the anterior eye part Ea.

In the event of failure in specifying the characteristic position, the controller 210 controls the camera moving part described above in response to reception of information from the characteristic position specifying part 2312 to move the anterior eye cameras 300A and 300B in the direction away from the supporter 440 and/or the direction outwards of the supporter 440. In the event of moving the anterior eye cameras 300A and 300B in the direction away from the supporter 440, the distance between the anterior eye cameras 300A and 300B and the subject (the eye E) increases, becoming capable of photographing a wider scope of the subject's face and possibility that the eye E is positioned in a range suitable for photography by means of the anterior eye cameras 300A and 300B increases. In the event of moving the anterior eye cameras 300A and 300B in the direction outwards of the supporter 440, the anterior eye cameras 300A and 300B move toward the subject's ear, increasing possibility that the eye E is positioned in a range suitable for photographing by the anterior eye cameras 300A and 300B. Moreover, by combining the movements in these two directions, possibility that the eye E is positioned in a range suitable for photographing is further enhanced.

After completion of movement of the anterior eye cameras 300A and 300B, moving-image photography by the anterior eye cameras 300A and 300B, specification of the center of the pupil, and determination for successful specification are carried out again. It is possible, in the event in which this routine is repeated a predetermined number of times, to execute control for transferring to automatic alignment by means of the alignment target or manual alignment.

When specification of the characteristic position is succeeded, the image judging part 232 judges whether or not the image corresponding to the anterior eye part Ea is within a predetermined area of the frame. In this operation example, this judgment is executed using the characteristic position specified by the characteristic position specifying part 2312. When it is judged that the image of the anterior eye part Ea is not positioned within the predetermined area of the frame, the anterior eye cameras 300A and 300B are moved again. On the other hand, when it is judged that the image of the anterior eye part Ea is positioned within the predetermined area of the frame, the three-dimensional position calculator 2313 calculates three-dimensional position of the center of the pupil of the eye E based on the positions of the anterior eye cameras 300A and 300B and the characteristic position specified by the characteristic position specifying part 2312 regarding the pair of frames. Then, based on the calculated three-dimensional position, the controller 210 controls the optical system driver 2A so as to match the optical axis of the optical system with the axis of the eye E and such that the distance of the optical system from the eye E becomes the specific working distance. The alignment is performed in such a way.

Instead of referring to anterior-eye images acquired by the anterior eye cameras 300A and 300B or in addition to referring to reference of anterior-eye images, alignment may be carried out by means of the alignment target described above. Alternatively, alignment may be carried out manually while referring to an observation image of the anterior eye part Ea.

(S3: OCT Measurement of Cornea)

After completion of alignment, the ophthalmologic apparatus 1 performs OCT measurement of the cornea (anterior eye part Ea) of the eye E. This OCT measurement is performed based on the examination conditions set in the preparation described above. Note that anterior-eye-part photography started in Step S1 is still ongoing in this stage.

(S4: Storing OCT Data and Anterior-Eye Images)

The controller 210 stores OCT data acquired in Step S3 and anterior-eye images acquired when performing the OCT measurement in the storage 212.

The OCT data includes at least information (first optical path length information) indicating optical path length of the optical system applied to the OCT measurement of the cornea. Since measurement optical path length is variable in the present embodiment, the first optical path length information includes information indicating measurement optical path length.

The OCT data may include any of conditions applied to the OCT measurement of the cornea (e.g. scanning pattern). The OCT data may include data acquired by the OCT measurement of the cornea (e.g. A-scan profile, image data of a cross sectional image, etc.). The OCT data may include data obtained by processing data acquired by the OCT measurement of the cornea (e.g. data obtained by analysis, data processed for display, etc.).

Anterior-eye images to be stored are images acquired at at least any of the timings among immediately before, during and immediately after the OCT measurement of the cornea. Here, an error between a timing of the OCT measurement of the cornea and a timing of acquiring the anterior-eye images is permissible as long as it is within a range in which it is generally recognized that eye movement does not occur, for example.

Anterior-eye images to be stored may include a pair of frames acquired by the anterior eye cameras 300A and 300B substantially simultaneously or may include a frame acquired by one of the anterior eye cameras 300A and 300B.

(S5: Changing Optical Path Length)

Next, the controller 210 changes optical path length of the optical system for changing a subject for OCT measurement from cornea to fundus. In the present example, measurement optical path length is changed by controlling the optical-path-length changing part 41. Amount of change in the optical path length may be a default value. Alternatively, the optical path length may be changed with reference to an image of the eye E such as photograph images acquired by the anterior eye cameras 300A and 300B, an observation image acquired by the optical system, etc.

(S6: Has Anterior-Eye Image Substantially the Same as that Acquired at the Time of Cornea Measurement Been Acquired?)

In this stage, anterior-eye-part photography is still ongoing. The controller 210 transmits frames input from the anterior eye cameras 300A and 300B to the image specifying part 233 successively. Further, the controller 210 transmits the anterior-eye image stored in the storage 212 in Step S4 to the image specifying part 233. This anterior image is used as an reference image (first image) in the comparison processing executed by the image specifying part 233. As described above, the reference image(s) is a frame(s) acquired by one or both of the anterior eye cameras 300A and 300B.

The image specifying part 233 compares the frames successively input from the controller 210 with the reference image. This comparison processing is repeatedly executed on the frames successively input until substantially the same frame as the reference image (second image) is specified (S6: NO). In response to specification of the second image, the image specifying part 233 transmits a signal to the controller 210 (S6: YES).

When the second image is not specified even if the comparison processing is executed for a preset period of time or when the second image is not specified even if the comparison processing is executed by the preset number of times, the ophthalmologic apparatus 1 may perform notification. This notification is performed by the controller 210 displaying a message showing that the second image is not specified on the display 241 or by the controller 210 controlling an audio output part (illustration omitted) to output an alarm, for example. The user recognizes such notification and may adjust position of the optical system manually, for example.

(S7: OCT Measurement of Fundus)

As described above, in response to specification of substantially the same frame as the reference image (second image), the image specifying part 233 transmits a signal to the controller 210. The controller 210 receives this signal and controls the ophthalmologic apparatus 1 to perform OCT measurement of the fundus Ef. This OCT measurement is performed based on the examination conditions set in the preparation described above. Note that anterior-eye-part photography started in Step S1 may be still ongoing in this stage or may have been ended already.

The controller 210 stores OCT data acquired by the OCT measurement of the fundus Ef in the storage 212. The OCT data includes at least information (second optical path length information) indicating optical path length of the optical system applied to the OCT measurement of the fundus Ef. This OCT data may include other data described above. The controller 210 may store an anterior-eye image acquired at the time of the OCT measurement of the fundus Ef together with the OCT data. The anterior-eye image may be the second image specified in the Step S6, for example.

(S8: Calculating Intraocular Distance)

The controller 210 reads out the first optical path length information obtained in Step S4 and the second optical path length information obtained in Step S7 from the storage 212 and transmits them to the distance calculator 234. The distance calculator 234 calculates distance (intraocular distance) between the first site included in the scanning region of the OCT measurement of the cornea and the second site included in the scanning region of the OCT measurement of the fundus Ef.

Processing executed by the distance calculator 234 in the present example is explained. It is assumed that the first site is corneal apex, second site is fundus center and intraocular distance is axial length. In the present example, OCT measurement of the fundus Ef is performed at the time of acquisition of an anterior-eye image substantially the same as the anterior-eye image acquired at the time of OCT measurement of the cornea. Further, it is assumed that OCT measurement of the cornea is performed in the state in which the corneal apex (first site) substantially coincides with a coherence gate and OCT measurement of the fundus Ef is performed in the state in which the fundus center (second site) substantially coincides with a coherence gate. Note that the other cases are described in Operation example 2 below.

Under such assumptions, the distance calculator 234 calculates (absolute value of) difference |L1−L2| between first measurement optical path length L1 indicated by the first optical path length and second measurement optical path length L2 indicated by the second optical path length. This calculation includes processing of subtracting smaller one of the two optical path lengths from larger one or processing of calculating the difference of the two optical path lengths and taking its absolute value, for example. The value of the difference thus calculated is treated as the objective intraocular distance (axial length).

In the present example, measurement optical path length is changed by moving the corner cube of the optical-path-length changing part 41. Therefore, information indicated by the first and second optical path length information may be position information of this corner cube. This position information is obtained based on content of control by the controller 210 (such as the number of pulses of controlling pulses) or is detected by a position sensor, for example. The distance calculator 234 calculates, as intraocular distance (axial length), a value "2×|P1−P2|/n" obtained by dividing, by intraocular refractive index n, a doubled value of the difference between position P1 of the corner cube indicated in the first optical path length information and position P2 indicated in the second optical path length information. The value n of the refractive index is known and may be a standard value (such as the value of Gullstrand schematic eye) or a measured value of the eye E.

(OPERATION EXAMPLE 2)

The flowcharts shown in FIGS. 7A and 7B are referred to. Also, FIGS. 7C and 7D are referred to. The present example describes an example of operation to which Auto-Z is applied.

(S11: Commencing Photography of Anterior Eye Part)

Firstly, FIG. 7A is referred to. This step may be performed in the same way as Step S1 in the operation example 1, for example.

(S12: Alignment)

This step may be performed in the same way as Step S2 in the operation example 1, for example.

(S13: Auto-Z Targeted at Corneal Apex)

After completing the alignment of Step S12, the controller 210 performs Auto-Z for matching the corneal apex with a coherence gate. The Auto-Z is carried out in the same way as above. The controller 210 stores information indicating success/failure in the Auto-Z in the storage 212.

In the case of failure in the Auto-Z, position adjustment of images within frames of OCT image may be performed by a manual operation, for example. Note that it is sufficient that an image corresponding to the corneal apex is included in the frames.

(S14: OCT Measurement of Cornea)

This step may be performed in the same way as Step S3 in the operation example 1, for example.

(S15: Storing OCT Data and Anterior-Eye Images)

This step may be performed in the same way as Step S4 in the operation example 1, for example.

(S16: Changing Optical Path Length)

This step may be performed in the same way as Step S5 in the operation example 1, for example.

(S17: Auto-Z targeted at Fundus Center)

Next, the controller 210 performs Auto-Z for matching the fundus center with a coherence gate. The Auto-Z is carried out in the same way as above. The controller 210 stores information indicating success/failure in the Auto-Z in the storage 212.

In the case of failure in the Auto-Z, position adjustment of images within frames of OCT image may be performed by a manual operation, for example. Note that it is sufficient that an image corresponding to the fundus center is included in the frames.

(S18: Has Anterior-Eye Image Substantially the Same as that Acquired at the Time of Cornea Measurement Been Acquired?)

This step may be performed in the same way as Step S6 in the operation example 1, for example.

(S19: OCT Measurement of Fundus)

This step may be performed in the same way as Step S7 in the operation example 1, for example.

(S20: Storing OCT Data)

This step may be performed in the same way as the storing processing of OCT image in Step S4 in the operation example 1, for example. Then, FIG. 7B is refereed to.

(S21: Has Auto-Z Been Successful?)

The controller 210 may recognizes success/failure in the respective Auto-Z by referring to information stored in Steps S13 and S17. When both Auto-Z are successful (S21: YES), the processing is shifted to Step S25. When one or both Auto-Z is failed (S21: NO), the processing is shifted to Step S22.

(S22: Calculating Difference of Optical Path Lengths)

When one or both Auto-Z in Steps S13 and S17 is failed (S21: NO), the distance calculator 234 calculates (absolute value of) difference |L1-L2| between first measurement optical path length L1 indicated by the first optical path length and second measurement optical path length L2 indicated by the second optical path length in the same way as Step S8 in the operation example 1. This calculation may be performed by calculating the doubled value of the difference between position of the corner cube of the optical-path-length changing part 41 at Step S14 and position at Step S19, for example.

(S23: Calculating Displacement from Coherence Gate)

Next, the distance calculator 234 calculates displacement of the corneal apex from the coherence gate in the OCT measurement of Step S14 and displacement of the fundus center from the coherence gate in the OCT measurement of Step S19.

Calculation of displacement of the corneal apex is explained with reference to FIG. 7C. Note that although explanation is given with reference to OCT image here, it is also possible to calculate displacement based on detection signals of interference light acquired by OCT measurement or based on arbitrary signals or images obtained by processing the detection signals.

Now, FIG. 7C illustrates an OCT image G1 generated based on the OCT measurement of Step S14. This corneal OCT image G1 includes a pixel A1 corresponding to the corneal apex (corneal apex pixel). It is assumed that center position in the z-direction corresponds to the coherence gate in the frame of the corneal OCT image G1 (this is denoted by coherence gate position C1). Position of coherence gate in a frame is not limited to this; however, this position is known in all cases.

To begin with, the distance calculator 234 analyzes the corneal OCT image G1 to specify the corneal apex pixel A1. This analysis may include specification of group of pixels corresponding to corneal surface (front surface of cornea) based on pixel values and specification of a pixel located at a furthermost position in the −z-direction among the group of pixels, for example. As another example, this analysis includes processing of comparing pixel values of group of pixels located on a line orthogonal to the z-direction in a frame (that is, a line extending in the right-left direction in a frame) with a pixel value corresponding to cornea from the upper side to the lower side in order and specifying the first pixel having the pixel value corresponding to cornea. As a further example, when OCT measurement is performed in the state in which alignment is matched, this analysis includes specification of group of pixels corresponding to corneal surface (front surface of cornea) based on pixel values and specification of a pixel located on a line bisecting a frame in the direction orthogonal to the z-direction (that is, in the right-left direction of the frame).

Next, the distance calculator 234 calculates distance D1 between the corneal apex pixel A1 specified in the preceding stage and the coherence gate position C1. This calculation may include processing of obtaining a perpendicular line down from the corneal apex pixel A1 to the coherence gate position C1, counting the number of pixels on this perpendicular line and multiplying the number of the pixels by a preset pixel interval (corresponding to distance in the real space), for example. The processing of obtaining the perpendicular line may include processing of obtaining a line segment that connects the corneal apex pixel A1 and the coherence gate position C1 and extends in the z-direction, for example. The distance thus obtained corresponds to the displacement of the corneal apex from the coherence gate. As described above, the displacement includes amount and direction of displacement. In the example shown in FIG. 7C, displacement amount is the distance D1 and displacement direction is −z-direction (direction away from the fundus Ef).

Calculation of displacement of the fundus center is explained with reference to FIG. 7D. This processing may be executed similarly to the calculation of displacement of the corneal apex. A symbol G2 in FIG. 7D indicates an OCT image generated based on OCT measurement of Step S19 (fundus OCT image). Further, a symbol A2 indicates the fundus center and a symbol C2 indicates the coherence gate position. A symbol D2 indicates displacement of the fundus center A2 from the coherence gate C2. In the example shown in FIG. 7D, displacement amount is distance D2 and displacement direction is +z-direction (direction away from the cornea).

(S24: Calculating Intraocular Distance Based on Difference of Optical Path Lengths and Displacement of Images)

The distance calculator 234 calculates intraocular distance (axial length) based on the difference (ΔL) of the optical path lengths calculated in Step S22 as well as the displacement (ΔA1) of the corneal apex from the coherence gate and/or the displacement (ΔA2) of the fundus center from the coherence gate calculated in Step S23.

In the case of FIGS. 7C and 7D, since the displacement direction of the corneal apex is in the direction away from the fundus Ef and the displacement direction of the fundus center is in the direction away from the cornea, intraocular distance (axial length) is obtained by adding both displacements of the corneal apex and the fundus center to the difference of the optical path lengths: ΔL+ΔA1+ΔA2. In general, displace amounts are added when displacement direction of one site is the direction away from the other site, and displace amounts are subtracted when displacement direction of one site is the direction approaching to the other site. This is the end of the processing in the case of failure in Auto-Z of Step S13 and/or Step S17.

(S25: Calculating Intraocular Distance Based on Optical Path Lengths)

On the other hand, when both Auto-Z are successful in Steps S13 and S17 (S21: YES), the distance calculator 234 calculates intraocular distance (axial length) in the same way as Step S8 in the operation example 1.

(OPERATION EXAMPLE 3)

The flowchart shown in FIG. 8 is referred to. The present example describes an example of operation in which automatic alignment with reference image is performed.

(S31: Commencing Photography of Anterior Eye Part)

This step may be performed in the same way as Step S1 in the operation example 1, for example.

(S32: Alignment)

This step may be performed in the same way as Step S2 in the operation example 1, for example.

(S33: OCT Measurement of Cornea)

This step may be performed in the same way as Step S3 in the operation example 1, for example.

(S34: Storing OCT Data and Anterior-Eye Images)

This step may be performed in the same way as Step S4 in the operation example 1, for example. Note that anterior-eye images stored here will be used for automatic alignment of Step S36.

(S35: Changing Optical Path Length)

This step may be performed in the same way as Step S5 in the operation example 1, for example.

(S36: Automatic Alignment)

The controller 210 reads out the anterior-eye image stored in Step S34. The controller 210 (and the data processor 230) uses this anterior-eye image as a reference image to carry out Automatic alignment. This automatic alignment includes: calculation of displacements of frames from the reference image regarding the respective frames (anterior-eye images) successively input from the anterior eye cameras 300A and 300B; and movement of the optical system so as to cancel the calculated displacements, for example.

The calculation of displacements of the frames with respect to the reference image includes known image processing for calculating displacement between two images and may include any of extraction of characteristic points, image subtraction, affine transformation, image correlation, etc., for example.

The movement of the optical system is carried out by the controller 210 controlling the optical system driver 2A based on the calculation result of displacements of the frames from the reference image. Note that "cancelling a displacement" indicates that the optical system is moved by (−Δx, −Δy) when displacement is (Δx, Δy). Thereby, the optical system is positioned at a location at which substantially the same anterior-eye image as the reference image is acquired. Note that because a living eye moves randomly, repetition of the alignment processing described above realizes that the optical system is moved in chase of movement of the eye E (Automatic tracking).

(S37: Has Anterior-Eye Image Substantially the Same as that Acquired at the Time of Cornea Measurement Been Acquired?)

This step may be performed in the same way as Step S6 in the operation example 1, for example.

(S38: OCT Measurement of Fundus)

This step may be performed in the same way as Step S7 in the operation example 1, for example. The automatic alignment (automatic tracking) of Step S36 may have been ended already or may be still ongoing at the commencement timing of OCT measurement of the fundus Ef (S39: Calculating Intraocular Distance)

This step may be performed in the same way as Step S8 in the operation example 1, for example.

[Effects]

Effects of the ophthalmologic apparatus according to the present embodiment are explained.

The ophthalmologic apparatus according to the present embodiment includes a photographing part, an optical system, a changing part, a controller and a calculator (the distance calculator 234, for example).

The photographing part (the anterior eye cameras 300A and 300B, for example) photographs an eye from two or more different directions. The optical system (the optical system illustrated in FIGS. 1 and 2, for example) splits light from a light source (the light source unit 101, for example) into measurement light and reference light and detects interference light of returned light of the measurement light from the eye and the reference light. The changing part (the optical-path-length changing part 41, for example) changes optical path length of the measurement light. Note that the changing part may have a function that changes optical path length of the reference light. Further, the changing part may be configured to change both optical path lengths of the measurement light and the reference light.

The controller (the controller 210 (and the data processor 230), for example) controls the photographing part to perform photography and controls the optical system to perform first detection when first optical path length is set by the changing part. In addition, the controller controls the optical system to perform second detection when second optical path length is set and a second image is acquired by the photographing part, wherein the second image is substantially the same as a first image having acquired by the above photography.

In the example described above, the first optical path length corresponds to the optical path length set for performing OCT measurement of cornea. Further, the photography corresponds to the anterior-eye-part photography performed together with the OCT measurement of cornea. Further, the first detection corresponds to the OCT measurement of cornea. Further, the second optical path length corresponds to the optical path length set for performing OCT measurement of fundus. Further, the second detection corresponds to the OCT measurement of fundus. These are merely examples, and the first optical path length may be optical path length for performing OCT measurement of fundus or other sites and the second optical path length may be optical path length for performing OCT measurement of cornea or other sites. Further, an image acquired by the photographing is not limited to an anterior-eye image and may be an image of fundus or other sites.

The calculator calculates distance between a first site of the eye through which the measurement light has passed in the first detection and a second site through which the measurement light has passed in the second detection based on the first and second optical path lengths.

Although axial length is obtained in the example described above, configuration is not limited to this and the distance calculated may be distance between an arbitrary site depicted in an OCT image based on the first detection and an arbitrary site depicted in an OCT image based on the second detection. In calculation of distance between such two sites, addition and/or subtraction are/is used in the case in which relative displacement of these sites is only displacement in the z-direction. On the other hand, trigonometry as well as addition and/or subtraction are used in the case in which relative displacement of these sites includes displacement in the x-direction and/or displacement in the y-direction. For example, when composing displacement in the x-direction and/or displacement in the y-direction and displacement in the z-direction, Pythagorean theorem may be used.

According to the embodiment thus configured, intraocular distance may be measured without preparing optical configurations for forming two reference optical paths. Further, the ophthalmologic apparatus of the embodiment is configured so as to, even if position and/or orientation of the eye are changed between the first and second detections, perform the second detection (OCT measurement) at the timing of acquisition of the second image that is substantially the same as the first image acquired by the photography performed together with the first detection (OCT measurement); therefore, disadvantage that measurement accuracy of intraocular distance is deteriorated due to the change of position etc. of the eye is solved. Accordingly, the ophthalmologic apparatus of the embodiment is capable of measuring intraocular distance with high accuracy and without increasing size and complexity of the apparatus.

The ophthalmologic apparatus of the embodiment may acquire time-series images by the photographing part when the second optical path length is set. Further, the controller may include a specifying part that compares still images successively acquired as the time-series images with the first image to specify the second image. In addition, the controller may control to perform the second detection in response to an event in which the second image is specified by the specifying part.

According to such a configuration, it is possible to specify the second image, that is, to detect the timing at which an image substantially the same as the first image is acquired. It is considered that measurement accuracy may be improved by setting photographing intervals (such as frame intervals) of the time-series images.

The calculator of the embodiment may calculate difference between the first and second optical path lengths as the distance between the firs and second sites when each of the first and second sites corresponds to a coherence gate.

On the other hand, when at least one of the first and second sites corresponds to a location apart from a coherence gate, the calculator of the embodiment may execute the following processing: calculation of difference between the first and second optical path lengths; calculation of displacement between the location apart from the coherence gate (location(s) of the first and/or second sites) and the coherence gate; and calculation of the distance between the first and second sites based on the above difference and the above displacement.

According to the processing carried out with reference to such coherence gates, the distance between the first and second sites may be measured with high accuracy.

The ophthalmologic apparatus of the embodiment may include a moving mechanism that moves the optical system. If this is the case, the following configuration may be adopted: the photographing part acquires time-series images; the controller calculates displacement between still images successively acquired as the time-series images with the first image; the controller controls the moving mechanism so as to cancel the displacement calculated: and the controller controls the optical system to perform second detection (OCT measurement) while executing this movement control or after this movement control.

According to such a configuration, automatic alignment (automatic tracking) may be performed so as to acquire the second image substantially the same as the first image having been acquired by the photography carried out together with the first detection (OCT measurement).

The controller of the embodiment may execute processing for arranging the first site at a coherence gate based on the result of the first detection. In addition to this or instead of this, the controller of the embodiment may execute processing for arranging the second site at a coherence gate based on the result of the second detection. Such processing corresponds to Auto-Z in the examples described above.

According to such a configuration, it is possible to arrange the first and/or second sites referred for distance measurement at the coherence gate. The coherence gate is a location in which interference sensitivity becomes the highest and an image depicted there is high definition. Therefore, high-definition images of the first and/or second site may be acquired. Thereby, it is possible to achieve further improvement of accuracy of distance measurement. Without having to match the first and/or second sites with coherence gate exactly, processing of arranging the first and/or second sites at neighborhood thereof improves accuracy in comparison with the case in which concerned function (Auto-Z) is not provided.

<Second Embodiment>

The first embodiment describes a configuration that, in order to measure distance (such as axial length) between a first site (such as corneal apex) of an eye and a second site (such as fundus center), performs control so as to acquire substantially the same photograph images in both of the case in which the first optical path length is set for the optical system and the case in which the second optical path length is set.

In contrast, the second embodiment performs first photography and first detection in the state in which first optical path length is set instead of performing control for acquiring substantially the same photograph images, and further, the second embodiment performs second photography and second detection in the state in which second optical path length is set and then obtains distance between a first and second sites of an eye. Distance calculation of the present embodiment refers to first and second images acquired by the first and second photography in addition to the first and second optical path lengths.

[Configuration]

Figure 9:
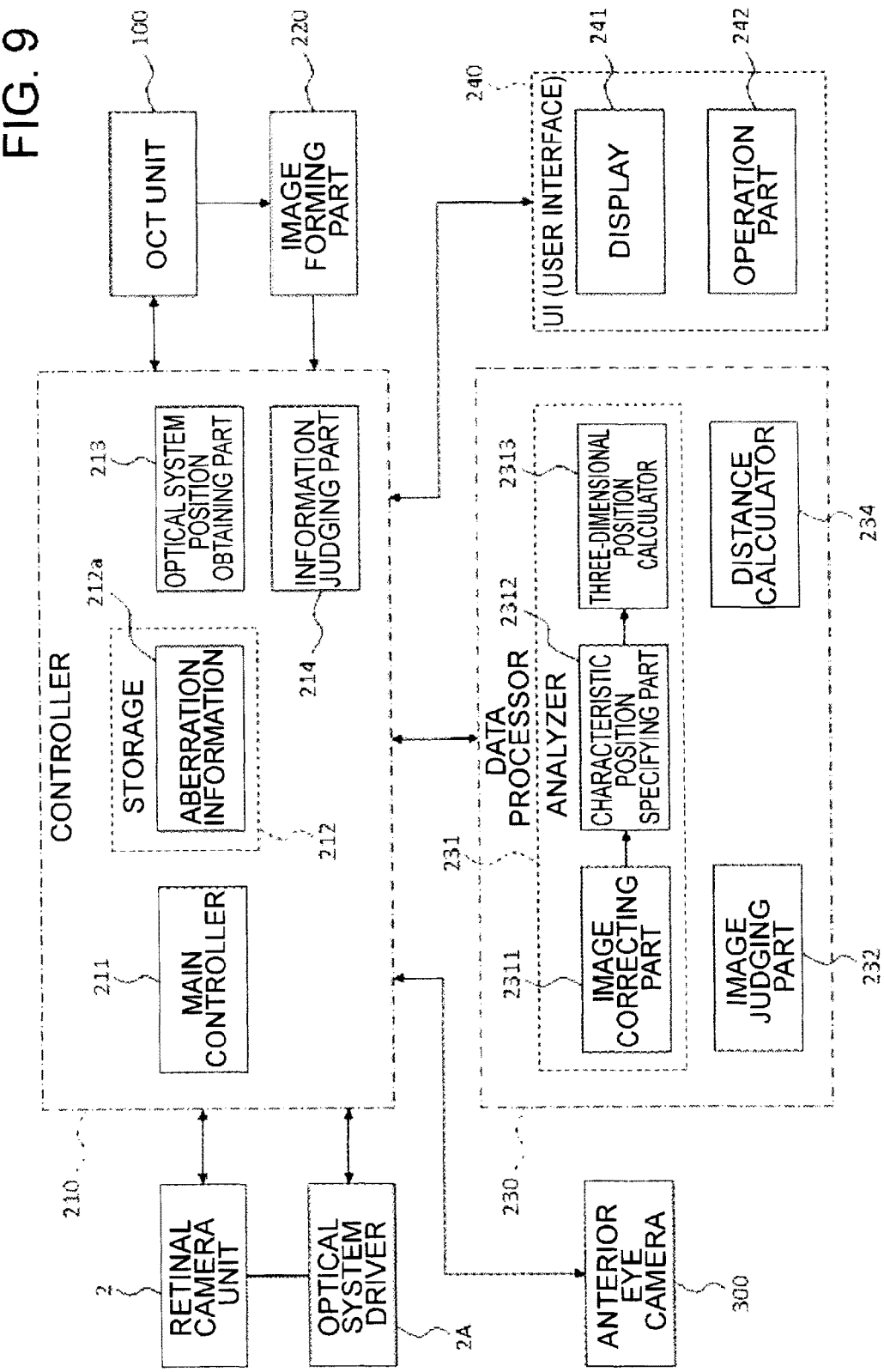
FIG. 9 is a schematic diagram showing an example of the configuration of an ophthalmologic apparatus according to an embodiment.

An ophthalmologic apparatus of the present embodiment includes hardware configurations similar to those in the first embodiment (refer to FIGS. 1, 2, 4A and 4B). Further, the ophthalmologic apparatus of the present embodiment does not need to execute control for acquiring substantially the same photograph images and so it does not need to include configurations for this control. FIG. 9 illustrates a configuration example of the ophthalmologic apparatus of the present embodiment. This configuration includes components shown in FIG. 3 of the first embodiment except for the image specifying part 233.

[Operations]

Figure 10:
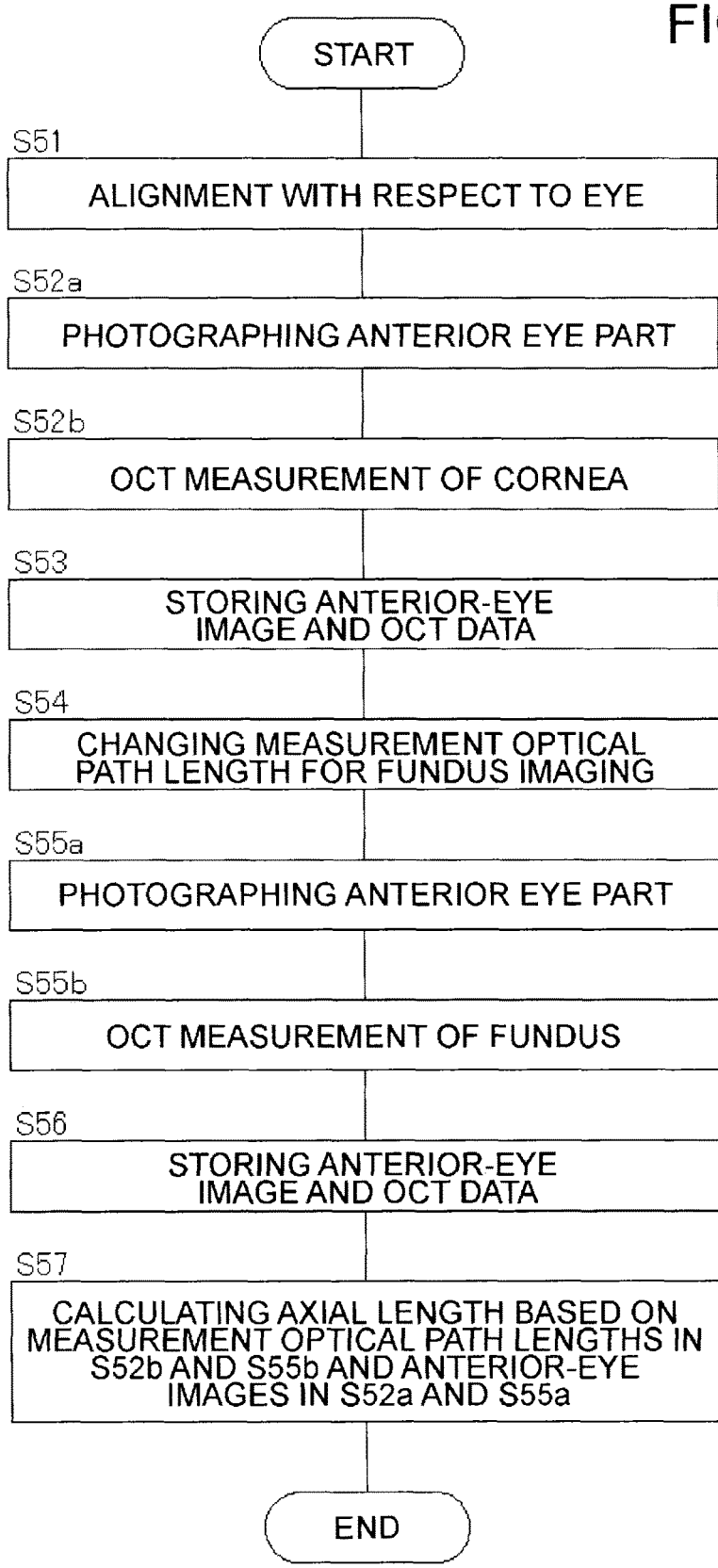
FIG. 10 is a flowchart showing an operation example of an ophthalmologic apparatus according to an embodiment.

Operations of the ophthalmologic apparatus of the present embodiment are described. An operation example of the ophthalmologic apparatus 1 is shown in FIG. 10. Auto-Z and/or automatic alignment (automatic tracking) described in the first embodiment may be adopted. It is assumed that registration of patient and setting of examination conditions have been done already.

(S51: Alignment)

This step may be performed in the same way as Step S2 in the operation example 1 of the first embodiment, for example.

(S52a: Photographing Anterior Eye Part)

Photography of the anterior eye part Ea is performed by means of the anterior eye cameras 300A and 300B in Step S52a. A photograph image acquired may be a still image or time-series image (such as moving image).

The steps S52a and S52b may be performed in arbitrary order. Further, these steps may be performed in parallel. For example, as in the first embodiment, acquisition of a time-series image may be started before the alignment of step S51, and further, anterior-eye-part photography and OCT measurement of step S52b may be performed in parallel after the alignment. It is to be desired that difference of timings between steps S52a and S52b is small enough not to receive influence of eye movement. For example, the difference of timings may be zero (that is, these steps are performed simultaneously).

(S52b: OCT Measurement of Cornea)

This step may be performed in the same way as Step S3 in the operation example 1 of the first embodiment, for example.

(S53: Storing Anterior-Eye Image and OCT Data)

This step may be performed in the same way as Step S4 in the operation example 1 of the first embodiment, for example.

(S54: Changing Optical Path Length)

This step may be performed in the same way as Step S5 in the operation example 1 of the first embodiment, for example.

(S55a: Photographing Anterior Eye Part)

This step may be performed in the same way as Step S52a, for example.

(S55b: OCT Measurement of Fundus)

This step may be performed in the same way as Step S7 in the operation example 1 of the first embodiment, for example.

(S56: Storing Anterior-Eye Image and OCT Data)

This step may be performed in the same way as Step S4 in the operation example 1 of the first embodiment, for example.

(S57: Calculating Intraocular Distance)

The distance calculator 234 calculates intraocular distance (axial length) based on the anterior-eye image and OCT data stored in step S53 and the anterior-eye image and OCT data stored in step S56.

When each end of a line segment corresponding to intraocular distance (corneal apex and fundus center in the case of axial length) corresponds to a position in a frame corresponding to a coherence gate, the distance calculator 234 executes the following processing: (1) calculation of displacement between the anterior-eye image (first image) stored in step S53 and the anterior-eye image (second image) stored in step S56; (2) calculation of difference between measurement optical path length (first optical path length) included in the OCT data stored in step S53 and measurement optical path length (second optical path length) included in the OCT data stored in step S56; (3) calculation of intraocular distance based on the displacement calculated in (1) and the difference calculated in (2).

Judgment whether or not the end of the line segment corresponds the position corresponding to the coherence gate may be carried out in the same way as in the first embodiment, for example.

Image processing in (1) may be the same as the comparison processing executed by the image specifying part 233 of the first embodiment, for example. This image processing uses any of image correlation, extraction of characteristic points, image subtraction, affine transformation, etc. to calculate displacement between the two anterior-eye images, for example. The displacement obtained by this image processing includes at least displacement in direction (xy-direction) orthogonal to the z-direction and may include displacement in the z-direction.

Calculation in (2) may be the same as the processing executed by the distance calculator 234 of the first embodiment, for example. The difference obtained by this calculation corresponds to displacement in the z-direction regarding two sites of the eye E.

Calculation in (2) includes processing of composing the displacement in the xy-direction obtained from the image processing of (1) and the displacement (difference) in the z-direction obtained from the calculation of (2) by using the Pythagorean theorem etc. From such processing, intraocular distance corresponding to three-dimensional displacement of the two sites of the eye E is obtained. In the case of obtaining displacement in the z-direction as well from the image processing of (1), composition processing is executed by taking this displacement in the z-direction into account.

When one or both end of the line segment corresponding to intraocular distance (corneal apex and fundus center in the case of axial length) is not located at the position in the frames corresponding to the coherence gate, the distance calculator 234 executes the following processing, for example: (1) calculating displacement (first displacement) between the anterior-eye image (first image) stored in step S53 and the anterior-eye image (second image) stored in step S56; (2) for each site of the eye E located in a position away from the coherence gate (that is, for each site corresponding to the end(s) described above), calculating displacement (second displacement) between the position of this site and the coherence gate; (3) calculating difference between measurement optical path length (first optical path length) included in the OCT data stored in step S53 and measurement optical path length (second optical path length) included in the OCT data stored in step S56; (4) calculating intraocular distance based on the first displacement calculated in (1), the second displacement calculated in (2) and the difference calculated in (3).

The image processing in (1) and calculation in (3) may be the same as in the case in which both sites are located at positions corresponding to the coherence gates. The displacement obtained by the image processing in (1) includes at least displacement in direction (xy-direction) orthogonal to the z-direction and may include displacement in the z-direction. The difference obtained by the calculation in (3) corresponds to displacement in the z-direction regarding two sites of the eye E.

The calculation in (2) may include analysis of OCT images to specify a pixel corresponding to a target site of the eye E and calculation of distance between the specified pixel and group of pixels corresponding to coherence gate, for example. The second displacement obtained from this calculation is displacement in the z-direction.

The calculation in (4) may include: calculation of sum or difference of the displacement (second displacement) in the z-direction obtained from the calculation in (2) and the displacement (difference) in the z-direction obtained from the calculation in (3); and composition of this sum or difference in the z-direction and the displacement (first displacement) in the xy-direction obtained from the image processing in (1) by means of the Pythagorean theorem etc., for example. Thereby, intraocular distance corresponding to three-dimensional displacement between two sites of the eye E is obtained.

The ophthalmologic apparatus of the present embodiment may be capable of performing automatic alignment and/or Auto-Z in the same way as the first embodiment. Automatic alignment is carried out by moving the optical system before step S55a so as to acquire an anterior-eye image substantially the same as the anterior-eye image stored in step S53, for example. Auto-Z is carried out by changing optical path length difference between the measurement optical path and the reference optical path so as to arrange a target site of the eye E (corneal apex, fundus center, for example) at a coherence gate before step S52a and/or step S55a, for example.

[Effects]

Effects of the ophthalmologic apparatus according to the present embodiment are explained.

The ophthalmologic apparatus according to the present embodiment includes a photographing part, an optical system, a changing part, a controller and a calculator (the distance calculator 234, for example).

The photographing part (the anterior eye cameras 300A and 300B, for example) photographs an eye from two or more different directions. The optical system (the optical system illustrated in FIGS. 1 and 2, for example) splits light from a light source (the light source unit 101, for example) into measurement light and reference light and detects interference light of returned light of the measurement light from the eye and the reference light. The changing part (the optical-path-length changing part 41, for example) changes optical path length of the measurement light. Note that the changing part may have a function that changes optical path length of the reference light. Further, the changing part may be configured to change both optical path lengths of the measurement light and the reference light.

The controller (the controller 210 (and the data processor 230), for example) controls the photographing part to perform first photography and the optical system to perform first detection when first optical path length is set by the changing part. Further, the controller controls the photographing part to perform second photography and the optical system to perform second detection when second optical path length is set.

The calculator calculates distance between first and second sites of the eye based on a first image acquired by the first photography, a second image acquired by the second photography, the first optical path length and the second optical path length. The first and second sites are included in areas (scanning areas) through which the measurement light has passed in the first and second detections, respectively.

According to the embodiment thus configured, intraocular distance may be measured without preparing optical configurations for forming two reference optical paths. Further, the ophthalmologic apparatus of the embodiment is capable of detecting displacement of the eye based on the image (first image) acquired by the first photography performed together with the first detection and the image (second image) acquired by the second photography performed together with the second detection even if position and/or orientation of the eye are changed between the first and second detections. Further, this ophthalmologic apparatus is capable of obtaining intraocular distance by taking the detected displacement into account. From such a configuration, disadvantage that measurement accuracy of intraocular distance is deteriorated due to the change of position etc. of the eye is solved. Accordingly, the ophthalmologic apparatus of the embodiment is capable of measuring intraocular distance with high accuracy and without increasing size and complexity of the apparatus.

When each of the first and second sites corresponds to a coherence gate, the calculator of the embodiment may perform the following processing: calculating displacement between the first and second images; calculating difference between the first and second optical path lengths; and calculating the distance between the first and second sites based on the displacement and the difference described above.

On the other hand, when at least one of the first and second sites corresponds to a location apart from a coherence gate, the calculator of the embodiment may perform the following processing: calculating first displacement between the first and second images; calculating second displacement between the location apart from the coherence gate (that is, the location of the first site, the location of the second site) and the coherence gate; calculating difference between the first and second optical path lengths; and calculating the distance between the first and second sites based on the first displacement, the second displacement and the difference described above.

According to such processing executed by referring to coherence gate, distance between the first and second sites may be obtained with high accuracy.

The ophthalmologic apparatus of the embodiment may include a moving mechanism that moves the optical system. If this is the case, the following configuration may be adopted: the photographing part acquires time-series images; the controller calculates displacement between still images successively acquired as the time-series images with the first image; the controller controls the moving mechanism so as to cancel the displacement calculated: and the controller controls the optical system to perform second detection (OCT measurement) while executing this movement control or after this movement control.

According to such a configuration, automatic alignment (automatic tracking) may be performed so as to acquire the second image substantially the same as the first image having been acquired by the photography carried out together with the first detection (OCT measurement).

The controller of the embodiment may execute processing for arranging the first site at a coherence gate based on the result of the first detection. In addition to this or instead of this, the controller of the embodiment may execute processing for arranging the second site at a coherence gate based on the result of the second detection. Such processing corresponds to Auto-Z in the examples described above.

According to such a configuration, it is possible to obtain high-definition images of the first and/or second sites. Thereby, it is possible to achieve further improvement of accuracy of distance measurement. Without having to match the first and/or second sites with coherence gate exactly, processing of arranging the first and/or second sites at neighborhood thereof improves accuracy in comparison with the case in which concerned function (Auto-Z) is not provided.

<Modified Example>

The embodiments described above are merely examples. One who intends to implement the present invention may arbitrarily modify (omission, replacement, addition, etc.) within the scope of the invention.

In the above embodiments, measurement optical path length is changed by changing position of the optical-path-length changing part 41; however, it may be configured to change reference optical path length. A configuration for changing the reference optical path length may include a refection mirror (reference mirror) provided in the optical path of the reference light and a driving mechanism that moves the reference mirror along the travelling direction of the reference light.

The technology described in the embodiments may be applied to any medical field other than ophthalmology or any field other than medical field. The technology described in the embodiments is effective in the case in which an object moves (such as movement, deformation, etc.), in particular. For example, the technology may be applied to measurement of heart and digestive organs, measurement of tissues of animals, etc.

Computer programs for realizing the above embodiments can be stored in any kind of recording medium that can be read by a computer. As this recording medium, for example, a semiconductor memory, an optical disk, a magneto-optic disk (CD-ROM, DVD-RAM, DVD-ROM, MO, and so on), and a magnetic storage (a hard disk, a floppy disk (TM), ZIP, and so on) can be used.

What is claimed is:

1. An ophthalmologic apparatus comprising:
a photographing part that photographs an eye from two or more different directions;
an optical system that splits light from a light source into measurement light and reference light and detects interference light of returned light of the measurement light from the eye and the reference light;
a changing part that changes optical path length of the measurement light and/or the reference light;
a controller that controls the photographing part to perform photography and the optical system to perform first detection when first optical path length is set by the changing part and controls the optical system to perform second detection when second optical path length is set and a second image that is substantially the same as a first image acquired by the photography is acquired by the photographing part; and
a calculator that calculates distance between a first site of the eye through which the measurement light has passed in the first detection and a second site of the eye through which the measurement light has passed in the second detection based on the first and second optical path lengths.

2. The ophthalmologic apparatus of claim 1, wherein the photographing part acquires time-series images when the second optical path length is set, and
the controller comprises a specifying part that compares still images successively acquired as the time-series images with the first image to specify the second image, and controls to perform the second detection in response to specification of the second image by the specifying part.

3. The ophthalmologic apparatus of claim 2, wherein the calculator calculates difference between the first and second optical path lengths as the distance when each of the first and second sites corresponds to a coherence gate.

4. The ophthalmologic apparatus of claim 2, wherein when at least one of the first and second sites corresponds to a location apart from a coherence gate, the calculator calculates difference between the first and second optical path lengths, calculates displacement between the location apart from the coherence gate and the coherence gate, and calculates the distance based on the difference and the displacement.

5. The ophthalmologic apparatus of claim 2, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

6. The ophthalmologic apparatus of claim 2, wherein the controller executes one or both of processing for arranging the first site at a coherence gate based on the result of the first detection and processing for arranging the second site at a coherence gate based on the result of the second detection.

7. The ophthalmologic apparatus of claim 1, wherein the calculator calculates difference between the first and second optical path lengths as the distance when each of the first and second sites corresponds to a coherence gate.

8. The ophthalmologic apparatus of claim 7, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

9. The ophthalmologic apparatus of claim 7, wherein the controller executes one or both of processing for arranging the first site at a coherence gate based on the result of the first detection and processing for arranging the second site at a coherence gate based on the result of the second detection.

10. The ophthalmologic apparatus of claim 1, wherein when at least one of the first and second sites corresponds to a location apart from a coherence gate, the calculator calculates difference between the first and second optical path lengths, calculates displacement between the location apart from the coherence gate and the coherence gate, and calculates the distance based on the difference and the displacement.

11. The ophthalmologic apparatus of claim 10, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

12. The ophthalmologic apparatus of claim 10, wherein the controller executes one or both of processing for arranging the first site at a coherence gate based on the result of the first detection and processing for arranging the second site at a coherence gate based on the result of the second detection.

13. The ophthalmologic apparatus of claim 1, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

14. The ophthalmologic apparatus of claim 13, wherein the controller executes one or both of processing for arranging the first site at a coherence gate based on the result of the first detection and processing for arranging the second site at a coherence gate based on the result of the second detection.

15. The ophthalmologic apparatus of claim 1, wherein the controller executes one or both of processing for arranging the first site at a coherence gate based on the result of the first detection and processing for arranging the second site at a coherence gate based on the result of the second detection.

16. An ophthalmologic apparatus comprising:
a photographing part that photographs an eye from two or more different directions;
an optical system that splits light from a light source into measurement light and reference light and detects interference light of returned light of the measurement light from the eye and the reference light;
a changing part that changes optical path length of the measurement light and/or the reference light;
a controller that controls the photographing part to perform first photography and the optical system to perform first detection when first optical path length is set by the changing part and controls the photographing part to perform second photography and the optical system to perform second detection when second optical path length is set; and
a calculator that calculates distance between a first site of the eye through which the measurement light has passed in the first detection and a second site of the eye through which the measurement light has passed in the second detection based on a first image acquired by the first photography, a second image acquired by the second photography, the first optical path length and the second optical path length.

17. The ophthalmologic apparatus of claim 16, wherein when each of the first and second sites corresponds to a coherence gate, the calculator calculates displacement between the first and second images, calculates difference between the first and second optical path lengths, and calculates the distance based on the displacement and the difference.

18. The ophthalmologic apparatus of claim 17, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

19. The ophthalmologic apparatus of claim 17, wherein the controller executes one or both of processing for arranging the first site at a coherence gate based on the result of the first detection and processing for arranging the second site at a coherence gate based on the result of the second detection.

20. The ophthalmologic apparatus of claim 16, wherein when at least one of the first and second sites corresponds to a location apart from a coherence gate, the calculator calculates first displacement between the first and second images, calculates second displacement between the location apart from the coherence gate and the coherence gate, calculates difference between the first and second optical path lengths, and calculates the distance based on the first displacement, the second displacement and the difference.

21. The ophthalmologic apparatus of claim 20, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

22. The ophthalmologic apparatus of claim 20, wherein the controller executes one or both of processing for arranging the first site at a coherence gate based on the result of the first detection and processing for arranging the second site at a coherence gate based on the result of the second detection.

23. The ophthalmologic apparatus of claim 16, further comprising a moving mechanism that moves the optical system, wherein
the photographing part is capable of acquiring time-series images,
the controller calculates displacement between still images successively acquired as the time-series images with the first image, controls the moving mechanism so as to cancel the displacement calculated, and controls the optical system to perform second detection while executing this control or after this control.

24. The ophthalmologic apparatus of claim 16, wherein the controller executes one or both of processing for arranging the first site at a coherence gate based on the result of the first detection and processing for arranging the second site at a coherence gate based on the result of the second detection.

* * * * *